United States Patent

Suzuki et al.

[11] Patent Number: 4,870,175
[45] Date of Patent: Sep. 26, 1989

[54] 6-SUBSTITUTED ALKOXY-2-OXO-1,2-DIHYDROQUINOXALINE DERIVATIVES

[75] Inventors: Yukio Suzuki; Masao Yaso; Katumi Nisimura; Kenzi Saeki; Noriyasu Takayanagi; Tetsu Saito; Eiichi Hayashi, all of Shizuoka, Japan

[73] Assignee: Toyo Jozo Kabushiki Kaisha, Shizuoka, Japan

[21] Appl. No.: 253,546

[22] Filed: Oct. 5, 1988

[30] Foreign Application Priority Data

Oct. 5, 1987 [JP] Japan .................. 62-251264
Aug. 24, 1988 [JP] Japan .................. 63-210346

[51] Int. Cl.⁴ .................. C07D 241/44; C07D 401/12; C07D 403/12; A61K 31/495
[52] U.S. Cl. .................. 544/354; 548/253; 560/22; 544/391; 546/226
[58] Field of Search .................. 544/354

[56] References Cited

U.S. PATENT DOCUMENTS 4,167,512 9/1979 Lai .................. 544/354
4,296,114 10/1981 Appleton et al. .................. 544/354
4,466,916 8/1984 Lai et al. .................. 544/354
4,636,246 1/1987 Plath et al. .................. 544/354

Primary Examiner—Mark L. Berch
Assistant Examiner—E. Bernhardt
Attorney, Agent, or Firm—Young & Thompson

[57] ABSTRACT

A compound of the formula

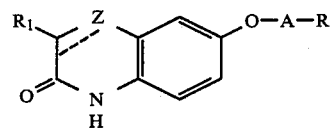

wherein Z is N or NH,---is a single or double bond, $R_1$ is hydrogen, $C_{1-20}$ alkyl or optionally substituted phenyl, A is lower alkylene, R is carboxyl, lower alkoxycarbonyl,

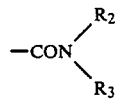

or 1-cycloalkyl-tetrazole-5-yl, $R_2$ is lower alkyl, hydroxy-lower alkyl or optionally substituted phenyl-lower alkyl, $R_3$ is lower alkyl or cycloalkyl, or $R_2$ and $R_3$ together constitute

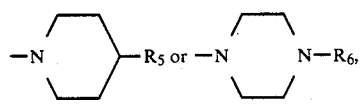

and $R_5$ and $R_6$ are hydrogen or optionally substituted phenyl, or a pharmacologically acceptable salt thereof, has platelet aggregation inhibitory activity and/or cyclic AMP/phosphodiesterase inhibitory activity.

1 Claim, No Drawings

6-SUBSTITUTED ALKOXY-2-OXO-1,2-DIHYDROQUINOXALINE DERIVATIVES

FIELD OF THE INVENTION

This invention relates to novel 6-substituted alkoxy-2-oxo-1,2-dihydroquinoxaline derivatives having platelet aggregation inhibitory activity and/or cyclic AMP/-phosphodiesterase inhibitory activity which are therefore useful as antithrombotic drugs or circulatory drugs.

DISCUSSION OF THE PRIOR ART

Hitherto-known quinoxaline derivatives having antithrombotic activity are: 1-diethylaminoethyl-2-oxo-3-(benzyl or substituted benzyl)-1,2-dihydroxyquinoxalines (Japan. Pat. Publ. No. 46-11183 and Japan. Pat. Unexam. Publ. No. 56-97226); 1-non-substituted or lower alkyl-3-substituted carbamoyloxymethyl-2-oxo-1,2-dihydroquinoxalines (Japan. Pat. Unexam. Publ. No. 49-24981); and $N^2$-(2,3-dioxoquinoxaline-6-yl) sulfonyl-L-arginineamide derivatives (Japan. Pat. Unexam. Publ. No. 54-100342).

Furthermore, among pharmacologically active 2-oxoquinoxaline derivatives, in which the benzene ring side chain is replaced by substituted alkoxy, which are useful for the treatment of cardiac or circulatory diseases, 5-or 8-[2-hydroxy-3-(substituted alkyl-amino- or substituted piperidino-)-propoxy]-3-non-substituted-, methyl- or hydroxymethyl-2-oxo-1,2-dihydroquinoxaline derivatives are known (Japan. Pat. Unexam. Publ. No. 55-162783).

OBJECT OF THE INVENTION

The object of the invention is to find excellent pharmaceuticals in this field having greater activities.

SUMMARY OF THE INVENTION

We have achieved the above object in that we have found that the hereinbelow described 3-non-substituted, alkyl or phenyl-6-substituted alkoxy-2-oxo-1,2-dihydroquinoxaline derivatives show platelet aggregation inhibitory activity and/or phosphodiesterase inhibitory activity to a pharmaceutically interesting degree.

DETAILED DESCRIPTION

The present invention provides compounds of the formula

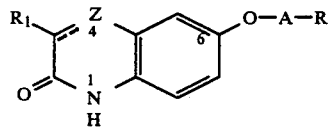
(1)

wherein Z is N or NH, --- is a single or double bond, $R_1$ is hydrogen, $C_{1-20}$ alkyl or optionally substituted phenyl, A is lower alkylene, R is carboxyl, lower alkoxycarbonyl,

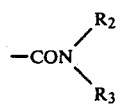

or 1-cycloalkyl-tetrazole-5-yl, $R_2$ is lower alkyl, hydroxy-lower alkyl or optionally substituted phenyl-lower alkyl, $R_3$ is lower alkyl or cycloalkyl, or $R_2$ and $R_3$ together constitute

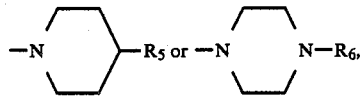

and $R_5$ and $R_6$ are hydrogen or optionally substituted phenyl, or a pharmacologically acceptable salt thereof.

The compounds [1] can be provided as salts thereof. The salts are pharmacologically acceptable non-toxic salts thereof. Examples of salts are salts of inorganic acids such as hydrochloride, sulfate or phosphate, and organic acids such as acetate, propionate, butyrate, glycolate, gluconate, malate, tartrate, succinate, mandelate, glutamate, aspartate, methanesulfonate or toluenesulfonate. Other known salts can be used.

The compound [1] can be produced by the following processes: Process A:

A process for the production of compound [1] wherein Z is N, --- is a double bond and R is lower alkoxy carbonyl or 1-cycloalkyl-tetrazole-5-yl (hereinafter designated as compound [1a]) of the formula

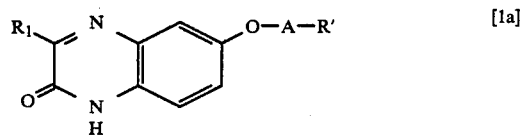
[1a]

wherein R' is alkoxycarbonyl or 1-cycloalkyl-tetrazole-5-yl.

The above compound [1a] can be produced by reducing and cyclizing a compound of the formula

[2]

wherein $R_7$ is lower alkyl, and $R_1$ and R' have the same meanings as hereinbefore, to obtain a compound of the formula

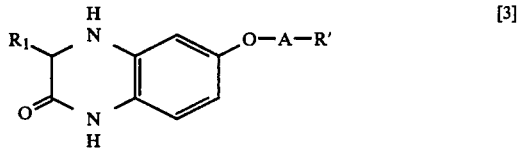
[3]

wherein $R_1$, R' and A have the same meanings as hereinbefore, which is then oxidized with an oxidizing agent.

In the compound [2] above, $R_1$ is hydrogen, $C_{1-20}$ alkyl or optionally substituted phenyl. Alkyl as used above is defined as saturated or unsaturated $C_{1-20}$ alkyl, which may be branched or unbranched. Examples are methyl, ethyl, propyl, isopropyl, butyl, isobutyl, sec-butyl, t-butyl, pentyl, isopentyl, hexyl, heptyl, octyl, nonyl, decyl, undecyl, dodecyl, tridecyl, tetradecyl, pentadecyl or hexadecyl. Optionally substituted phenyl, as used above, is defined as phenyl or phenyl substituted with $C_{1-3}$ lower alkyl, halogen, nitro or lower alkoxy.

A is lower alkylene, which is defined as optionally branched $C_{1-6}$ alkylene. Examples are methylene, ethylene, methylmethylene, propylene, isobutylene or pentalene.

In the compound [2] above, R' is lower alkoxycarbonyl or 1-cycloalkyl-tetrazole-5-yl. The lower alkoxy can be $C_{1-4}$ alkoxy such as methoxy, ethoxy, propoxy, isopropoxy, butoxy, isobutoxy, sec-butoxy or t-butoxy. The above cycloalkyl is $C_{5-7}$ cycloalkyl, preferably cyclohexyl. $R_7$ in the above is lower alkyl which is optionally branched $C_{1-4}$ alkyl such as methyl or ethyl.

The above compound [2] is a novel compound and can be produced by O-alkylating a compound of the formula

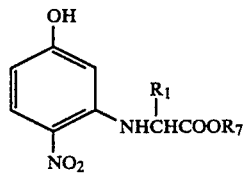

wherein $R_1$ and $R_7$ have the same meanings as hereinbefore, with a halide of the formula

 [5]

wherein X is halogen, and A and R' have the same meanings as hereinbefore, in a reaction medium.

The above compound [4] may be produced by the process in which a commercially available 3-fluoro-4-nitrophenol is reacted with α-amino acid of the formula

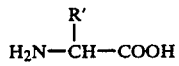

wherein $R_1$ has the same meaning as hereinbefore, in the presence of alkali, for example alkaline hydrogen carbonate such as sodium hydrogen carbonate or alkaline carbonate such as sodium carbonate or potassium carbonate, while refluxing with water containing a lower alkanol such as methanol or ethanol. Thereafter the reaction mixture is neutralized with hydrochloric acid to remove the reaction solvent, dried, then the lower alkanol is added thereto, and the compound is esterified by adding thionyl chloride.

Isolation of the product [4] can be performed by filtering off the insoluble material, removing the reaction solvent, thereafter dissolving the product with a water-immiscible organic solvent such as chloroform, drying the product, removing the solvent and further purifying the product by column chromatography using silica gel. The thus-obtained compound [4] is a novel compound.

The groups A and R' defined in the above halide [5] have the same definition as hereinbefore. Group X in the formula [5] hereinabove is halogen such as chlorine or bromine.

O-alkylation of the compound [4] with halide [5] is preferably performed after dissolving compound [4] in an alkanol solution (such as ethanol) of an alkali metal such as metallic sodium, and distilling off the ethanol to activate the hydroxyl group.

An example of a reaction solvent in the above O-alkylation is dimethyl formamide.

The above O-alkylation reaction preferably proceeds under heating. The reaction can be terminated when the maximum production of the compound [2] is achieved.

Isolation of the product [2] can be performed by distilling off the reaction solvent, dissolving the residue in a water-immiscible organic solvent such as chloroform, washing with dilute aqueous alkali, drying the organic layer and distilling off the solvent. Further purification can be performed by silica-gel chromatography using an elution solvent mixture such as benzene-ethyl acetate.

Reduction and cyclization of nitrobenzene derivative [2] can be performed by dissolving the compound [2] in a reaction solvent, for example a lower alkanol such as ethanol, adding thereto a reducing agent, which reduces the nitro group to amino, such as an excess of iron powder, and adding hydrogen chloride/lower alkanol while heating to complete the intramolecular cyclization.

Isolation of the product [3] can be performed by removing any insoluble material by filtration, distilling off the reaction solvent, dissolving the residue in a water-immiscible organic solvent such as chloroform, washing with dilute aqueous alkali, and drying to remove the solvent. In the above isolation procedure, part of product [3] is oxidized and the produced compound [1a] is mixed in the product. Product [3] can be isolated and purified by silica-gel chromatography using an elution solvent such as chloroform-methanol. However, in order to obtain compound [1a], product [3] mixed with compound [1a] can be treated preferably with an oxidizing agent to obtain product [1a] without a purification procedure. For example, an impure product [3] dissolved in benzene is heated, after adding dichlorodicyano benzoquinone, until the product [3] is consumed, and if required any insoluble material is dissolved by heating; then the solvent is removed and the residue is isolated and purified by silica-gel chromatography using an elution solvent of chloroform-methanol to obtain the product [1a].

Another method of oxidation of the product [3] is oxidation by aqueous hydrogen peroxide, in which the product [3] is oxidized in an ethanol solution.

In the above reaction-cyclization reaction, when the reaction mixture is filtered using a filter-aid and the concentrated filtration is left to stand, ferric chloride generated by the reaction of iron powder and hydrogen chloride acts as an oxidizing agent for the product [3], then all of the product [3] is converted to the product [1a] which can be purified by the same procedure as hereinabove.

Another method of reduction and cyclization is that compound [2] dissolved in a lower alkanol such as ethanol is subjected to catalytic hydrogenation under catalysis with Pd/C. The reaction proceeds at room temperature. The product [3] can be obtained by removing the catalyst and reaction solvent, thereafter purifying by the same procedure as above. The product [1a] can be obtained by oxidizing the product [3]. Process B:

A process for the production of compound [1] wherein Z is N, is double bond, and R is carboxyl, of the formula

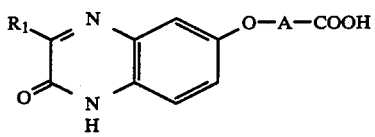

wherein $R_1$ and A have the same meanings as hereinbefore:

The above compound [1b] can be obtained by subjecting to de-esterification a compound [1a'] in which R' is lower alkoxycarbonyl

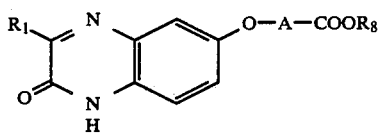

wherein $R_8$ is lower alkyl, and $R_1$ and A have the same meanings as hereinbefore.

The above de-esterification is performed by dissolving compound [1a'] in lower alkanol and treating it with alkali hydroxide such as KOH or NaOH. The reaction proceeds at room temperature and can be terminated when the compound [1a'] has been consumed.

Isolation of the product [1b] can be effected by adding water to the reaction mixture, acidifying by adding hydrochloric acid, filtering the precipitated crystals, washing with water and drying. Process C:

A process for the production of compound [1] wherein Z is N, is double bond, and R is

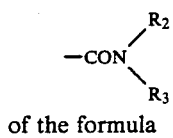

of the formula

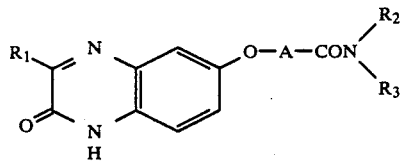

wherein $R_1$, $R_2$, $R_3$ and A have the same meanings as hereinbefore.

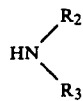 A compound [1c] can be produced by acid halogenating or anhydrating the compound [1b] and reacting with an amine of the formula

[6]

HN\
  \R_2
  /
  R_3 wherein $R_2$ and $R_3$ have the same meanings as hereinbefore.

The group $R_2$ in the above amine [6] is lower alkyl, hydroxy lower alkyl or optionally substituted phenyl-lower alkyl, and $R_3$ is lower alkyl or cycloalkyl, or $R_2$ and $R_3$ can together constitute

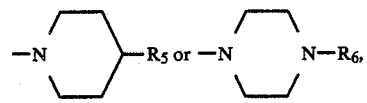

in which $R_5$ and $R_6$ are hydrogen or optionally substituted phenyl.

Examples of lower alkyl are optionally branched $C_{1-4}$ alkyl such as methyl, ethyl, propyl, isopropyl, butyl, isobutyl, sec-butyl or t-butyl. An example of hydroxy lower alkyl is hydroxy alkyl in which optionally substituted $C_{1-4}$ alkyl has a substituent hydroxy group, such as hydroxymethyl, 2-hydroxyethyl, 1-hydroxyethyl, 3-hydroxypropyl, 2-hydroxypropyl or 1-hydroxypropyl. The phenyl in the optionally substituted phenyl-lower alkyl is a phenyl which has as a substituent 1-3 lower alkyl, halogen, nitro or lower alkoxy.

The above cycloalkyl is $C_{5-7}$ cycloalkyl.

The optionally substituted phenyl having substituents $R_5$ and $R_6$ is a phenyl having as a substituent 1-3 lower alkyl, halogen, nitro or lower alkoxy.

Examples of the above amine [6] are diethylamine, N-methyl-cyclohexylamine, N-ethyl-cyclohexylamine, N-2-hydroxyethyl-cyclohexylamine, N-benzyl-cyclohexylamine, piperidine, 4-phenylpiperidine, piperazine, 4-phenylpiperazine or 4-(o-, m- or p-methoxyphenyl) piperazine.

An acid halide of the compound [1b] can be produced by a known halogenation with a known halogenating agent. Examples of halogenating agents are $SOCl_2$, $PCl_5$, $POCl_3$ or $SOBr_2$. Halogenation can be performed in a reaction solvent such as chloroform.

An acid anhydride of a compound [1b] can be produced by reacting a compound [1b] with a carboxylic acid halide such as pivaloyl chloride in a reaction solvent such as tetrahydrofuran or dimethylformamide in the presence of a tertiary organic amine such as triethylamine to form a mixed anhydride with a compound [1b] and carboxylic acid.

The thus-formed compound [1b] is converted to a reactive derivative and the said derivative is reacted with the above amine [6]. The reaction proceeds in general under ice cooling or at room temperature. Isolation of the product can be effected by mixing it with a water-immiscible organic solvent, washing with dilute alkaline solution, drying, removing the solvent and subjecting it to silica-gel column chromatography using as an elution system chloroform-methanol.

Another method of synthesis of the compound [1c] is as follows:

A compound of the formula

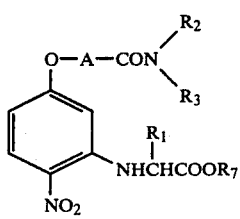

wherein $R_1$, $R_2$, $R_3$, $R_7$ and A have the same meanings as hereinbefore is reduced and subjected to cyclization, and oxidized by an oxidizing agent.

The above compound [7] can be produced by O-alkylating the compound [4] with a halide of the formula

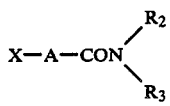 [8]

wherein $R_2$, $R_3$, A and X have the same meanings as hereinbefore, in a reaction medium.

The above reduction, cyclization and oxidation can be effected in the same way as of in the Process A.

Process D:

A process for the production of compound [1] wherein Z is NH, is single bond and R is lower alkoxycarbonyl or 1-cycloalkyl-tetrazole-5-yl, of the formula

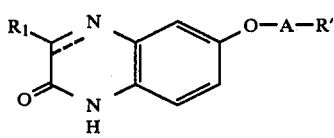 [1d]

wherein $R_7$ is lower alkoxycarbonyl or 1-cycloalkyl-tetrazol-5-yl, and $R_1$ and A have the same meanings as hereinbefore.

The above compound [1d] can be obtained by isolating and purifying the compound [A] hereinbefore. Process E:

A process for the production of compound [1] wherein Z is NH,═is single bond and R is carboxyl, of the formula

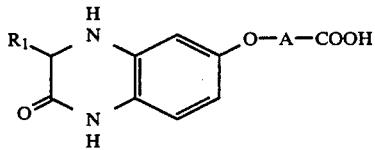 [1e]

wherein $R_1$ and A have the same meanings as hereinbefore:

The above compound [1e] can be obtained by subjecting to de-esterification a compound of the formula [1d'] in which R' is lower alkoxycarbonyl in the compound [1d].

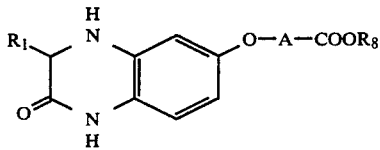 [1d']

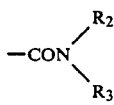

wherein $R_8$, $R_1$ and A have the same meanings as hereinbefore.

The above de-esterification is performed by dissolving compound [1d'] in lower alkanol and treating it with alkali hydroxide such as KOH or NaOH. The reaction proceeds at room temperature and can be terminated when the compound [1d'] has been consumed.

Isolation of the product [1e] can be effected by adding water to the reaction mixture, acidifying by adding hydrochloric acid, filtering the precipitated crystals, washing with water and drying. Process F:

A process for production of compound [1] wherein Z is NH,═is single bond, and R is

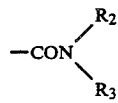

of the formula

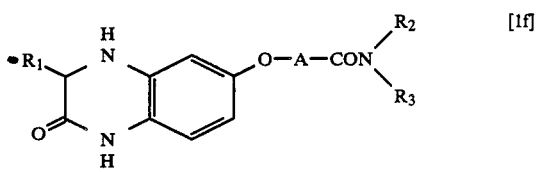 [1f]

wherein $R_1$, $R_2$, $R_3$ and A have the same meanings as hereinbefore.

Compound [1f] can be produced by acid halogenating or anhydrating compound [1e] and reacting it with amine [6].

The reaction conditions and isolation of the compound [1f] can be effected the same as in Process C. Another method of production of the compound [1f] is that the compound [7] is reduced and subjected to cyclization.

Reduction and cyclization can be effected the same way as in Process A.

Examples of the compounds of the present invention are given in Table 3.

Pharmacological Activity of the Invention

The pharmacological activity of the present compounds [1] is illustrated below. (1) Inhibitory action of cyclic AMP/phosphodiesterase:

A mixture of 2 mM $MgCl_2$/40 mM Tris-buffer (pH 7.5) 700 μl, enzyme solution (a crude enzyme fraction obtained from sonicated rabbit platelets) 100 μl, and a test sample solution (compound [1] dissolved in 50% aqueous methanol) 100 μl is incubated at 30° C. for 5 mins. 3', 5'-cyclic AMP 100 μl (50 μg) is added thereto and the mixture is further incubated for 40 mins. The reaction is stopped by heating 100° C. for 5 mins. The amount of 5'-AMP in the supernatant obtained by centrifugation at 3000 rpm for 5 mins. is measured using HPLC.

The results are shown in Table 1. As shown in that table, the compound of the present invention has cyclic AMP/phosphodiesterase inhibitory activity at 1–10 μg/ml.

TABLE 1

| Comp. No. | Inhibitory ratio (%) | | |
|---|---|---|---|
| | 1 μg/ml | 10 μg/ml | 100 μg/ml |
| 896 | 25.5 | 71.5 | 91.0 |
| 913 | 19.2 | 80.3 | |
| 914 | 18.1 | 34.3 | 54.4 |
| 915 | 37.2 | 77.7 | 85.1 |
| 916 | 47.3 | 78.0 | 85.7 |
| 917 | 16.6 | 59.3 | 87.7 |
| 918 | 19.8 | 61.0 | 87.9 |

TABLE 1-continued

| Comp. No. | Inhibitory ratio (%) | | |
|---|---|---|---|
| | 1 μg/ml | 10 μg/ml | 100 μg/ml |
| 919 | 23.9 | 65.2 | 92.4 |
| 920 | 42.9 | 81.7 | 75.1 |
| 921 | 49.8 | 84.5 | 93.0 |
| 922 | 61.7 | 88.1 | 91.1 |
| 923 | 43.7 | 81.8 | 92.4 |
| 924 | 24.6 | 63.5 | 70.2 |
| 925 | 5.3 | 26.4 | 71.3 |
| 927 | 10.5 | 47.7 | 76.1 |
| 929 | 11.2 | 53.9 | 88.5 |
| 931 | 25.3 | 74.3 | 86.4 |
| 938 | 17.9 | 63.1 | 88.2 |
| 945 | 44.3 | 83.5 | 88.9 |
| 946 | 78.7 | 92.5 | |
| 974 | 66.9 | 90.1 | |
| 948 | 62.9 | 87.9 | 92.7 |
| 949 | 40.9 | 53.7 | |
| 954 | 42.4 | 54.2 | |
| 955 | 44.2 | 82.3 | 93.0 |
| 956 | 83.9 | 92.9 | 95.0 |
| 957 | 71.4 | 90.7 | 94.0 |
| 958 | 69.9 | 91.4 | 93.7 |
| 959 | 43.4 | 80.5 | 91.0 |
| 960 | 34.8 | 61.7 | 87.4 |
| 964 | 43.8 | 78.8 | 90.5 |
| 965 | 68.9 | 87.3 | |
| 966 | 54.5 | 86.6 | 93.7 |
| 967 | 38.0 | 81.0 | 92.8 |
| 968 | 17.1 | 60.3 | |
| 969 | 72.7 | 82.5 | |
| 970 | 24.1 | 51.5 | |
| 971 | 84.4 | 93.0 | |
| 972 | 84.4 | 93.4 | |
| 973 | 37.6 | 42.2 | |
| 974 | 73.2 | 91.7 | |
| 975 | 59.5 | 88.9 | 93.5 |
| 976 | 51.1 | 84.5 | |
| 978 | 26.2 | 40.1 | |
| 986 | 66.2 | 80.5 | |
| 987 | 57.4 | 83.3 | 90.2 |
| 988 | 46.4 | 76.9 | |

(2) Platelet aggregation inhibition:

A rabbit platelet-rich plasma ($5 \times 10^5$/mm$^3$), to which was added 1/10 volume of a 3.8% sodium citrate solution, 216 μl, is incubated in an aggregometer at 37° C., 1000 rpm, for 3 mins. A test sample solution 12 μl (final concentration 10 μM) is added thereto and the mixture is further incubated for 3 mins., and collagen (aggregation agent) 2.5 μg/ml, ADP 2.5 μM, platelet activating factor (PAF) 0.05 μg/ml or 0.25 mM arachidonic acid (A.A.) 12 μl is added thereto as an aggregating agent, and the platelet aggregation activity is measured.

The results are shown in Table 2. As shown in that table, the compound of the present invention clearly shows platelet aggregation inhibitory activity at 10 μM.

TABLE 2

| Comp. No. | Inhibitory ratio (%) | | | |
|---|---|---|---|---|
| | Collagen | ADP | PAF | A.A. |
| 896 | 59.2 | 37.2 | 37.1 | 31.1 |
| 915 | 63.2 | 41.0 | 36.0 | 30.4 |
| 917 | 57.4 | 36.9 | 36.7 | 32.6 |
| 920 | 52.5 | 49.3 | 26.9 | 30.2 |
| 921 | 81.0 | 62.6 | 35.3 | 44.7 |
| 923 | 75.7 | 68.0 | 29.0 | 56.7 |
| 925 | 53.8 | 56.5 | 29.5 | 46.5 |
| 926 | 54.1 | 88.7 | 66.4 | 34.7 |
| 929 | 50.8 | 49.4 | 30.4 | 41.8 |
| 931 | 65.2 | | 44.3 | 34.0 |
| 945 | 54.2 | | | |
| 946 | 79.2 | 91.5 | 90.7 | 85.1 |
| 947 | 39.5 | 59.5 | 27.5 | 19.6 |
| 966 | 83.5 | | | |
| 972 | 70.5 | 63.6 | 56.3 | 48.7 |

As explained hereinabove, a compound [1] of the present invention or its pharmacologically acceptable salt has platelet aggregation inhibitory activity and/or cyclic AMP/phosphodiesterase inhibitory action, and is therefore useful in pharmaceuticals for use as antithrombotic drugs and circulatory drugs.

EXAMPLES

The following examples and referential examples are illustrative of the present invention but are not to be construed as limiting.

In the examples, the Rf value of silica-gel thin layer chromatography (TLC) is, if not specified, measured using the following carrier and developing solvent:
Carrier: silica gel, Kieselgel 60 F$_{254}$, Art 5715 (Merck)
Developer:
(a) chloroform-methanol (20:1)
(b) chloroform-methanol (10:1)
(c) benzene-ethyl acetate (5:1)

The physical properties of the compounds [1] obtained in the following examples are shown in Tables 12 and 13.

Referential Examples 1–10

N-(5-hydroxy-2-nitrophenyl)-amino acid ethyl ester:
3-fluoro-4-nitrophenol 30 mM, α-amino acid 50 mM and sodium hydrogen carbonate 100 mM were added to a mixture of ethanol 80 ml and water 20 ml and the mixture was refluxed. The reaction was terminated upon detecting the disappearance of a spot of phenol compound upon silica-gel thin layer chromatography (TLC). The reaction mixture was acidified by adding 6N HCl, concentrated in vacuo then the residue was dried completely. Ethanol 100 ml was added thereto and thionyl chloride 5 ml was added dropwise with ice cooling, then the mixture was stirred at room temperature overnight. Insoluble material was removed by filtration and the filtrate was concentrated in vacuo. The residue, dissolved in chloroform, was washed with water, dried by adding anhydrous magnesium sulfate and concentrated in vacuo. The residue was charged on a column of silica gel (WAKO Pure Chem. Co., Wakogel C-200) packed with benzene and eluted with benzene-ethyl acetate (50:1) to obtain N-(5-hydroxy-2-nitrophenyl)-amino acid ethyl ester.

The reaction scale (based on 3-fluoro-4-nitrophenol), the amino acid used, the reflux time and amount of yield of the product are shown in Table 4.

The physical properties of N-(5-hydroxy-2-nitrophenyl)-amino acid ethyl ester are shown in Table 5.

Referential Examples 11–20

N-[5-(3-ethoxycarbonyl) propoxy-2-nitrophenyl]-amino acid ethyl ester.

N-(5-hydroxy-2-nitrophenyl)-amino acid ethyl ester 10 mM obtained in Referential Examples 1–10 was added to and dissolved in metallic sodium 10 mM (0.23 g) dissolved in ethanol 50 ml, and the solvent was distilled off in vacuo. Dimethylformamide 100 ml and γ-bromobutyric acid ethyl ester 1.95 g were added to the residue, and the mixture was stirred at 100° C. The solvent was distilled off in vacuo and the residue was dissolved in chloroform. The chloroform solution was washed with dilute aqueous sodium carbonate. The aqueous layer was extracted with chloroform. The chloroform layers were combined, dried by adding anhydrous sodium sulfate and concentrated in vacuo. The residue was charged on a column of silica gel (C-200) packed with benzene, and eluted with benzene-ethyl acetate (50:1) to obtain the product.

The reaction scale [based on N-(5-hydroxy-2-nitrophenol]-amino acid used), the reflux time, the amount of silica gel used, and the amount and yield of the product are shown in Table 6.

The physical properties of N-[5-(3-ethoxycarbonyl) propoxy-2-nitrophenyl]-amino acid ethyl ester are shown in Table 7.

EXAMPLES 1-10

3-substituted-6-(3-ethoxycarbonylpropoxy)-2-oxo-1,2-dihydroquinoxaline:

Iron powder (4-5 equivalents) was added to N-[5-(3-ethoxycarbonyl) propoxy-2-nitrophenyl] amino acid ethyl ester (a starting material) dissolved in ethanol. Approx. 5-N HCl/ethanol solution was added dropwise slowly while refluxing and reacted for 3 hours. Insoluble material was removed by filtration, and the filtrate was washed with ethanol. The combined solutions (filtrate and washing) were concentrated in vacuo. The residue dissolved in chloroform was washed with water, and the aqueous layer was again extracted with chloroform. The combined chloroform layers were washed with dilute aqueous sodium carbonate, dried with anhydrous sodium sulfate and concentrated in vacuo to obtain a residue which is a mixture of the product hereinabove and 3-substituted-6-(3-ethoxycarbonylpropoxy)-2-oxo-1,2,3,4-tetrahydroquinoxaline.

An equimolar amount of dichlorodicyano benzoquinone (DDQ) was added to the said residue dissolved in benzene, and the mixture was refluxed for 3-4 hours. The reaction mixture was filtered hot to remove insoluble materials, washed completely with benzene, then concentrated in vacuo. The residue was charged on a column of silica gel (C-200) packed with chloroform, and purified by eluting with chloroform-methanol (20:1) to obtain the product.

In Table 8, the amounts of starting material, ethanol used, iron powder used, HCl/ethanol used, DDQ used, silica gel used, and the compound number of the product, its amount of yield and percentage yield are illustrated.

EXAMPLES 11-20

3-substituted-6-(3-carboxypropoxy)-2-oxo-1,2-dihydroquinoxaline:

2N-NaOH was added to a suspension of the ester 10 mM obtained in Referential Example 1-10 in ethanol 10 ml, then 2N-NaOH was added and the mixture was stirred at room temperature overnight. Water 30 ml was added to the reaction mixture, and the mixture was adjusted to approx. pH 2 by adding 6N-HCl. The precipitated crystals were filtered, washed completely with water and dried to obtain the product.

In Table 9, the compound number of the above ester, its amount used, the 2N-NaOH used, the product number and the amount obtained and yield are illustrated.

EXAMPLES 21-47

3-substituted-6-[3-N,N-di-substituted-aminocarbonyl) propoxy]-2-oxo-1,2-dihydroquinoxaline:

Carboxylic acid 2 mM obtained in Examples 11-20 was added to tetrahydrofuran 20 ml. An equimolar amount of triethylamine was added thereto, and there was further added dropwise an equimolar amount of pivaloyl chloride at −10° C., and the mixture was stirred at below −10° C. for 1 hour. An equimolar amount of amine was added at once to the obtained residue, and the mixture was stirred for 3 hours while gradually adjusting the temperature to room temperature. Chloroform was added to the reaction mixture, which was then washed with dilute aqueous potassium carbonate. The aqueous layer was further extracted with chloroform. The combined chloroform layers were dried by adding anhydrous sodium sulfate and concentrated in vacuo. The residue was charged on a column of silica gel (C-200, 70 g) and eluted with chloroform-methanol to obtain the product.

The number of the carboxylic acid, its amount used, the kind of amine, the amount used, the ratio of the solvent system chloroform-methanol, the number of the compound obtained, the amount obtained and the yield are shown in Table 10.

Referential Example 21

N-(5-hydroxy-2-nitrophenyl)-amino acetic acid methyl ester:

3-fluoro-4-nitrophenol 50 g (0.138 mole), glycine 48 g (0.637 mole) and sodium hydrogen carbonate 107 g (1.27 mole) were added to a mixture of ethanol 600 ml and water 100 ml and refluxed for 5 days. The solvent was distilled off in vacuo. The reaction mixture was acidified by adding dilute HCl and filtered. The filtrate was washed with dilute HCl and water, then dried in vacuo to obtain N-(5-hydroxy-2-nitrophenyl)-amino acetic acid as a yellow solid. Yield: 66.4 g (yield: 98%)

Thionyl chloride 30.84 g (260 mM) was added dropwise with ice cooling to N-(hydroxy-2-nitrophenyl)-amino acetic acid 45.78 g (0.216 mole) dissolved in methanol 500 ml for 30 mins.; then the mixture was stirred at room temperature for 22 hours. The reaction mixture was filtered, the filtered material was washed with methanol and dried to obtain the yellow solid product. The above filtrate was concentrated in vacuo and the precipitated material was washed with chloroform and dried. The solid materials thus obtained were combined to obtain the product 47.5 g (yield: 97%).

NMR (DMSO-$d_6$) δ (ppm); 3.71 (s, 3H, $CH_3$), 4.20 (d, 2H, $CH_2$), 6.04–6.29 (m, 2H, phenyl proton), 8.01 (d, 1H, phenyl proton), 8.50 (t, 1H, NH)

Mass (CI); 227 ($M^+ +1$) TLC; $Rf_b = 0.52$

Referential Example 22

N-[5-(3-ethoxycarbonyl) propoxy-2-nitrophenyl]-amino acetic acid methyl ester:

N-(5-hydroxy-2-nitrophenyl)-amino acetate methyl ester 8.31 g (37 mM) was dissolved in metallic sodium 0.85 g (37 mM) dissolved in methanol 100 ml, and the solvent was distilled off in vacuo. The residue was dissolved in dimethylformamide 80 ml and γ-bromo butyric acid ethyl ester 5.3 ml (37 mM) was added to the residue, and the mixture was stirred at 60° C. for 14 hours. The solvent was distilled off in vacuo. The residue was charged on a column of silica gel (C-200)

packed with chloroform and eluted with chloroform to obtain the product as yellow crystals.

Yield: 10.76 g (yield: 86%)

NMR (CDCl$_3$) δ (ppm); 1.27 (3, 3H, CH$_3$), 2.12 (q, 2H, CH$_2$), 2.51 (t, 2H, CH$_2$), 3.83 (s, 3H, CH$_3$), 4.00–4.28 (m, 6H, 3CH$_3$), 6.02–6.34 (m, 2H, phenyl proton), 8.16 (d, 1H, phenyl proton), 8.60 (t, 1H, NH)

Mass (Cl); 341 (M$^+$+1) TLC; Rf$_c$=0.44

EXAMPLE 48

6-(3-ethoxycarbonylpropoxy)-2-oxo-1,2,3,4-tetrahydroquinoxaline (compound 925):

N-[5-(3-ethoxycarbonyl) propoxy-2-nitrophenyl]-amino acetic acid methyl ester 2.42 g (7.1 mM) and iron powder 7.26 g were added to ethanol 100 ml.

Approx. 5-N HCl/ethanol solution was added thereto dropwise slowly while refluxing. The yellow color of the solution changed to colorless with generation of hydrogen gas. HCl/ethanol solution was added until consumption of the starting material was observed by the reaction mixture changing to colorless. The reaction mixture was decanted into chloroform-water. The organic layer was washed with aqueous sodium hydrogen carbonate and water, dried with anhydrous sodium sulfate and concentrated in vacuo. The residue was charged on a column of silica gel (C-200) packed with chloroform, and purified by eluting with chloroform-methanol (100:1) to obtain the compound 925.

Yield: 1.4 g (yield: 70%)

EXAMPLE 49

6-(3-ethoxycarbonylpropoxy)-2-oxo-1,2-dihydroquinoxaline (compound 914)

Dichlorodicyanobenzoquinone (DDQ) 4.5 g (19.8 mM) was added to the compound 925 5 g (18 mM) dissolved in benzene 300 ml with heating, and the mixture was refluxed for 3 hours. The reaction mixture was filtered hot and then the filtrate was concentrated in vacuo. The residue, dissolved in chloroform, was washed with water, dried by adding anhydrous sodium sulfate and concentrated in vacuo. The residue was charged on a column of silica gel (C-200) packed with chloroform, and purified by eluting with chloroform-methanol (300:1), (200:1) and (100:1), in this order to obtain the compound 914 as colorless crystals.

Yield: 4 g (yield: 81%)

EXAMPLES 50–54

6-[3-(N,N-di-substituted-aminocarbonyl)-propoxy]-2-oxo-1,2-dihydroquinoxaline:

2N-NaOH 6 ml was added to compound 914 (1 g, 3.6 mM, as the starting material) dissolved in 50% aqueous ethanol 50 ml and the mixture was stirred at room temperature for 1–1.5 hour. Dilute HCl was added to the reaction mixture to adjust it to an acidic pH, and the solvent was distilled off in vacuo. The residue was dried in vacuo to obtain crude 6-(3-carboxypropoxy)-2-oxo-1,2-dihydroquinoxaline (compound 938).

Dimethylformamide 50 ml and triethylamine 1 ml were added thereto, and there was further added dropwise pivaloyl chloride 0.45 ml, and the mixture was stirred at room temperature for 2 hours. Amine (4.3 mM) was added to the reaction mixture and the mixture was stirred at room temperature for 15 hours. The reaction mixture was concentrated in vacuo and chloroform was added thereto. Insoluble material was removed by filtration and the filtrate was concentrated in vacuo.

The residue was charged on a column of silica gel (C-200) packed with chloroform and eluted with chloroform-methanol (100:1) and (50:1) in this order to obtain the product.

The starting material, the kind of amine, the number of the compound obtained, the amount obtained and the yield are shown in Table 11.

Referential Example 23

N-[5-(3-ethoxycarbonyl) butoxy-2-nitrophenyl]-amino acetic acid methyl ester:

N-(5-hydroxy-2-nitrophenyl)-amino acetic acid methyl ester 15 g (66.4 mM) was dissolved in metallic sodium 1.83 g (797 mM) dissolved in methanol 100 ml, and the solvent was distilled off in vacuo. The residue was dissolved in dimethylformamide 150 ml and γ-bromo valeric acid ethyl ester 12.6 ml (79.7 mM) was added thereto and the mixture was stirred at 60° C. for 20 hours. The solvent was distilled off in vacuo. The residue, dissolved in chloroform, was filtered through Celite (tradename) to remove insoluble materials and concentrated in vacuo. The residue was charged on a column of silica gel (C-200) packed with chloroform and eluted with chloroform to obtain the product as yellow crystals.

Yield: 22.76 g (yield: 97%)

NMR (CDCl$_3$) δ (ppm); 1.26 (t, 3H, CH$_3$), 1.6–2.0 (m, 4H, 2CH$_2$), 2.39 (t, 2H, CH$_2$), 3.83 (s, 3H, CH$_3$), 3.9–4.3 (m, 6H, 3CH$_2$), 6.00 (d, 1H, phenyl proton), 6.27 (d.d, 1H, phenyl proton), 8.15 (d, 1H, phenyl proton).

Mass (Cl); 355 (M$^+$+1)

EXAMPLE 55

6-(4-ethoxycarbonylpropoxy)-2-oxo,1,2,3,4-tetrahydroquinoxaline (compound 927):

N-[5-(4-ethoxycarbonyl) propoxy-2-nitrophenyl]-amino acetic acid methyl ester 14.1 g (40 mM) and iron powder 42.3 g were added to ethanol 300 ml.

Approx. 5-N HCl/ethanol solution was added dropwise while refluxing. The yellow color of the solution changed to colorless with the generation of hydrogen gas. HCl/ethanol solution was added until consumption of the starting material, which was indicated by the reaction mixture changing to colorless. The reaction mixture was decanted into chloroform-water. The separated organic layer was washed with aqueous sodium hydrogen carbonate and water, dried with anhydrous sodium sulfate and concentrated in vacuo. The residue was charged on a column of silica gel (C-200) packed with chloroform, and purified by eluting with chloroform-methanol (100:1) to obtain the compound 927 as colorless crystals.

Yield: 9.8 g (yield: 84%)

EXAMPLE 56

6-(4-ethoxycarbonylpropoxy)-2-oxo-1,2-dihydroquinoxaline (compound 919)

Dichlorodicyanobenzoquinone (DDQ) 7.69 g (33.9 mM) was added to the compound 927 (9 g, 30.8 mM) dissolved in benzene 600 ml with heating, and the mixture was refluxed for 3 hours. The reaction mixture was filtered hot, then the filtrate was concentrated in vacuo. The residue dissolved in chloroform was washed with water, dried by adding anhydrous sodium sulfate and concentrated in vacuo. The residue was charged on a column of silica gel (C-200) packed with chloroform, and purified by eluting with chloroform-methanol (300:1), (200:1) and (100:1), in this order to obtain the compound 919 as colorless crystals.

Yield: 7.4 g (yield: 83%)

EXAMPLES 57–61

6-[4-(N,N-di-substituted-aminocarbonyl)-butoxy]-2-oxo-1,2-dihydroquinoxaline:

2N-NaOH 6 ml was added to the compound 919 (500 mg, 1.72 mM, as starting material) dissolved in 50% aqueous ethanol 50 ml and the mixture was stirred at room temperature for 1–1.5 hour. Dilute HCl was added to the reaction mixture to adjust it to acidic pH, and the solvent was distilled off in vacuo. The residue was dried in vacuo to obtain crude 6-(4-carboxybutoxy)-2-oxo-1,2-dihydroquinoxaline.

Dimethylformamide 50 ml and triethylamine 1 ml were added thereto, and there was further added dropwise pivaloyl chloride 0.45 ml, and the mixture was stirred at room temperature for 2 hours. Amine (4.3 mM) was added to the reaction mixture and the mixture was stirred at room temperature for 15 hours. The reaction mixture was concentrated in vacuo and chloroform was added thereto. Insoluble material was removed by filtration and the filtrate was concentrated in vacuo.

The residue was charged on a column of silica gel (C-200) packed with chloroform and eluted with chloroform-methanol (100:1) and (50:1) in this order to obtain the product.

The starting material, the kind of amine, the number of the compound obtained, the amount obtained and the yield are shown in Table 11.

Referential Example 24

N-[5-{3-(N-cyclohexyl-N-methyl-aminocarbonyl) propoxy}-2-nitrophenyl]-amino acetic acid methyl ester:

N-(5-hydroxy-2-nitrophenyl)-amino acetic acid methyl ester 10 g (44 mM) was added to metallic sodium 1.02 g (44 mM) dissolved in methanol 100 ml, and the solvent was distilled off in vacuo. The residue was dissolved in dimethylformamide 100 ml and N-cyclohexyl-N-methyl-4-chlorobutaneamide 9.6 g (44 mM) was added thereto and the mixture was stirred at 100° C. overnight. The reaction mixture was concentrated in vacuo. The residue, dissolved in chloroform, was washed with water, dried with anhydrous magnesium sulfate and concentrated in vacuo. The residue was charged on a column of silica gel (C-200) packed with benzene and eluted with benzene-ethyl acetate (5:1) and (3:1) to obtain the product as yellow crystals.

Yield: 10.3 g (yield: 58%)

NMR (CDCl$_3$) δ (ppm); 1.0–2.0 (m, 10H, 5CH$_2$), 2.15 (q. 2H, CH$_2$), 2.52 (t, 2H, CH$_2$), 2.84 (s, 3H, CH$_3$), 3.83 (s, 3H, CH$_3$), 4.0–4.2 (m, 4H, 2CH$_2$), 3.4–3.7, 4.2–4.6 (m, 1H, CH), 6.10 (d, 1H, phenyl proton), 6.29 (d.d, 1H, phenyl proton), 8.16 (d, 1H, phenyl proton), 8.60 (t, 1H, NH)

Mass (Cl); 408 (M$^+$+1) TLC; Rf=0.33 [benzene-ethyl acetate (1:1)]

EXAMPLE 62

6-[3-(N-cyclohexyl-N-methyl-aminocarbonyl) propoxy]-2-oxo-1,2,3,4-tetrahydroquinoxaline (compound 929):

N-[5-{3-(N-cyclohexyl-N-methyl-aminocarbonyl) propoxy}-2-nitrophenyl] amino acetic acid methyl ester 9 g (22 mM) and iron powder 27 g were added to ethanol 150 ml.

Approx. 5-N HCl/ethanol solution was added dropwise while refluxing. The yellow color of the solution changed to colorless with the generation of hydrogen gas. HCl/ethanol solution was added until consumption of the starting material was indicated by the change of the reaction mixture to colorless. The reaction mixture was decanted into chloroform-aqueous sodium hydrogen carbonate. The separated organic layer was washed with aqueous sodium hydrogen carbonate and water, dried with anhydrous sodium sulfate and concentrated in vacuo. The residue was charged on a column of silica gel (C-200) packed with chloroform, and purified by eluting with chloroform-methanol (100:1) to obtain the compound 929 as colorless crystals.

Yield: 7 g (yield: 91%)

Referential Example 25

5-[4-(1-cyclohexyl-tetrazole-5-yl) butoxy]-2-nitrophenyl-amino acetic acid methyl ester:

N-(5-hydroxy-2-nitrophenyl)-amino acetic acid methyl ester 5 g (22 mM) was added to metallic sodium 509 mg (22 MM) dissolved in methanol 30 ml, and the solvent was distilled off in vacuo. Dimethylformamide 100 ml was added to the residue and 1-chloro-4-(1-cyclohexyl tetrazole-5-yl) butane 5.36 g (22 mM) was added thereto and the mixture was stirred at 100° C. for 3 hours. The reaction mixture was concentrated in vacuo and the residue was charged on a column of silica gel (C-200) packed with benzene and eluted with benzene-ethyl acetate (15:1) to obtain the product as yellow crystals.

Yield: 2.9 g (yield: 30%)

NMR (CDCl$_3$) δ (ppm); 1.1–2.3 (m, 14H, 7CH$_2$), 2.93 (t, 2H, CH$_2$), 3.82 (s, 3H, CH$_3$), 3.9–4.4 (m, 5H, 2CH$_2$, CH), 5.99 (d, 1H, phenyl proton), 6.24 (d.d, 1H, phenyl proton), 8.11 (d, 1H, phenyl proton), 8.59 (t, 1H, NH)

Mass (Cl); 433 (M$^+$+1) TLC; Rf$_b$=0.62 Rf$_c$=0.05

EXAMPLE 63

6-[4-(1-cyclohexyl tetrazole-5-yl)-butoxy]-2-oxo-1,2,3,4-tetrahydroquinoxaline (compound 931):

N-[5-{4-(1-cyclohexyl tetrazole-5-yl) butoxy}-2-nitropheny] amino acetic acid methyl ester 1.9 g (4.4 mM) and 10% Pd/C catalyst 1.9 g were added to ethanol 500 ml.

The reaction mixture was stirred for 2 hours while bubbling hydrogen gas therethrough. The reaction mixture was filtered and the filtrate was concentrated in vacuo. The residue was charge don a column of silica gel (C-200) packed with chloroform, and purified by eluting with chloroform-methanol (200:1) to obtain the compound 931 as a colorless solid.

EXAMPLE 64

6-[4-(1-cyclohexyl-tetrazole-5-yl)-butoxy]-2-oxo-1,2-dihydroquinoxaline (compound 913):

N-[5-{4-(1-cyclohexyl-tetrazole-5-yl) butoxy}-2-nitrophenyl] amino acetic acid methyl ester 2 g (4.6 mM) and iron powder 6 g were added to ethanol 100 ml.

Approx. 5-N HCl/ethanol solution was added dropwise while refluxing until the starting material disappeared upon TLC. The reaction mixture was filtered through Celite and the filtrate was concentrated in vacuo. The thus-obtained residue was allowed to stand overnight. The compound 931 was thus converted to the compound 913 by oxidation. The residue was charged on a column of silica gel (C-200) packed with chloroform, and purified by eluting with chloroform-methanol (30:1) to obtain the compound 913 as colorless crystals.

Yield: 854 mg (yield: 50%)

EXAMPLE 65

3-methyl-6-[3-(N-cyclohexyl-N-ethylaminocarbonyl) propoxy]-2-oxo-1,2-dihydroquinoxaline (compound 1029):

3-methyl-6-(3-carboxypropoxy)-2-oxo-1,2-dihydroquinoxaline 2.0 mM obtained in Example 11 was added to tetrahydrofuran 20 ml. An equimolar amount of triethylamine was added thereto, and there was further added dropwise an equimolar amount of pivaloyl chloride at −10° C. and the mixture was stirred at below −10° C. for 1 hour. N-cyclohexylethylamine 0.3 ml was added at once to the obtained reaction mixture, and the mixture was stirred for 3 hours while gradually adjusting the temperature to room temperature. Chloroform was added to the reaction mixture, and the mixture was washed with dilute aqueous potassium carbonate. The aqueous layer was further extracted with chloroform. The combined chloroform layers were dried by adding anhydrous sodium sulfate and concentrated in vacuo. The residue was charged on a column of silica gel (C-200, 70 g) and eluted with chloroform-methanol (50:1) to obtain the compound 1029.

Yield: 0.47 g (yield: 63.3%)

Referential Example 26

2-{N-[5-(4-ethoxycarbonyl) butoxy-2-nitrophenyl]-amino-propionic acid ethyl ester:

2-[N-(5-hydroxy-2-nitrophenyl)]-amino propionic acid ethyl ester 12.7 g (50 mM) was added to metallic sodium 1.15 g (50 mM) dissolved in ethanol 150 ml, and the material was dried in vacuo. The residue was dissolved in dimethylformamide 300 ml and δ-bromovaleric acid ethyl ester 10.45 g (50 mM) was added thereto and the mixture was stirred overnight. The solvent was distilled off in vacuo. The residue, dissolved in chloroform, was washed with dilute aqueous potassium carbonate, dried with anhydrous sodium sulfate and concentrated in vacuo. The residue was charged on a column of silica gel (C-200, 120 g) packed with benzene and eluted with benzene-ethyl acetate to obtain the product.

Yield: 17.13 g (yield: 93.1%)

NMR (CDCl$_3$) δ (ppm); 1.27 (5, 3H, J=7), 1.28 (t, 3H, J=7), 1.60 (d, 3H, J=7), 1.6–2.0 (m, 4H), 2.39 (t, 2H, J=7), 3.8–4.4 (m, 7H), 6.04 (d, 1H, J=2.5), 6.25 (d.d, 1H, J=2.5, 10), 8.16 (1H, J=10), 8.54 (d, 1H, J=8)

Referential Example 27

2-{N-[5-(4-ethoxycarbonyl)-butoxy-2-nitrophenyl]}-amino-butyric acid ethyl ester:

In Referential Example 26, 2-[N-(5-hydroxy-2-nitrophenyl)]-aminopropionic acid ethyl ester was replaced by 2-[N-(5-hydroxy-2-nitrophenyl)]-aminobutyric ethyl ester (50 mM) to obtain the compound above.

Yield: 18.42 g (yield: 93.0%)

NMR (CDCl$_3$) δ (ppm); 1.06 (t, 3H, J=7), 1.26 (t, 3H, J=7), 1.28 (5, 3H, J=7), 1.6–2.2 (m, 6H), 2.39 (t, 2H, J=7), 3.9–4.4 (m, 7H), 6.06 (d, 1H, J=2.5), 6.25 (d.d, 1H, J=2.5, 10), 8.15 (d, 1H, J=10), 8.56 (d, 1H, J=8)

EXAMPLE 66

3-methyl-6-(ethoxycarbonylbutoxy)-2-oxo-1,2-dihydroquinoxaline (compound 1036):

2-{N-(4-ethoxycarbonyl) butoxy}-2-nitrophenyl] amino propionic acid ethyl ester 17.12 g (44.84 mM) and iron powder 11.6 g were added to ethanol 350 ml.

Approx. 5-N HCl/ethanol solution was added dropwise while refluxing, until the starting material disappeared. Insoluble material was removed by filtration and the filtrate was concentrated in vacuo. The residue, dissolved in chloroform, was washed with dilute hydrochloric acid and saturated sodium chloride solution, in this order, dried with anhydrous sodium sulfate and concentrated in vacuo. To the residue, dissolved in benzene 500 ml, was added DDQ 10.2 g, then the reaction mixture was refluxed for 2 hours.

Insoluble material was filtered off and the filtrate was concentrated in vacuo. The residue was charged on a column of silica gel (C-200, 250 g) packed with chloroform, and purified by eluting with chloroform-methanol (200:1) to obtain the compound 1036.

Yield: 8.99 g (yield: 66.0%)

EXAMPLE 67

3-ethyl-4-(ethoxycarbonyl butoxy)-2-oxo-1,2-dihydroquinoxaline (compound 1012):

In Example 66 2-{N-[5-(4-ethoxycarbonyl) butoxy-2-nitro-phenyl]}-amino-propionic acid ethyl ester was replaced by 2-{N-5-(4-ethoxycarbonyl) butoxy-2-nitrophenyl]}-amino-butyric acid ethyl ester 18.40 g (46.50 mM), iron powder 12.0 g and DDQ 11.1 g to obtain the compound 1012.

Yield: 9.12 g (yield: 61.7%)

EXAMPLE 68

3-methyl-6-(4-carboxybutoxy)-2-oxo-1,2-dihydroquinoxaline (compound 1037):

2N-NaOH solution 29.6 ml was added to the compound 1036 (8.99 g, 29.6 mM) suspended in methanol 29.6 ml and the mixture was stirred overnight. Water 88.8 ml was added to the reaction mixture, and the mixture was adjusted to pH 2 by adding 6N-HCl. Precipitated crystals were collected by filtration, washed completely with water and dried to obtain the compound 1037.

Yield: 7.89 g (yield: 96.6%)

EXAMPLE 69

3-ethyl-6-(4-carboxy butoxy)-2-oxo,1,2-dihydroquinoxaline (compound 1013):

2N-NaOH solution 28.0 ml was added to the compound 1012 (8.90 g, 28.9 mM) suspended in methanol 28.0 ml and the mixture was stirred overnight. Water 84.0 ml was added to the reaction mixture, and the mixture was adjusted to pH 2 by adding 6N-HCl. Precipitated crystals were collected by filtration, washed completely with water and dried to obtain the compound 1013.

EXAMPLE 70

3-methyl-6-[4-(N-cyclohexyl-N-2-hydroxyethylamino-carbonyl) butoxy]-2-oxo-1,2-dihydroquinoxaline (compound 1034):

Compound 1037 (5.0 mM) was added to tetrahydrofuran 20 ml. An equimolar amount of triethylamine was added thereto, and there was further added dropwise an equimolar amount of chloroisobutyl formate at −10° C. and the mixture was stirred at −10° C. for 1 hour. N-cyclohexyl-2-hydroxyethylamine 0.73 g was added at once, and the mixture was stirred for 3 hours while gradually adjusting its temperature to room temperature. Chloroform was added to the reaction mixture, and the mixture was washed with dilute aqueous potassium carbonate. The aqueous layer was further extracted with chloroform. The combined chloroform layers were dried by adding anhydrous sodium sulfate and concentrated in vacuo. The residue was charged on a column of silica gel (C-200, 120 g) and eluted with chloroform-methanol (30:1) to obtain the compound 1034.

Yield: 1.03 g (yield: 51.4%)

EXAMPLE 71

3-ethyl-6-[4-(N-cyclohexyl-N-2-hydroxyethylaminocarbonyl) butoxy]-2-oxo-1,2-dihydroquinoxaline (compound 1015):

In Example 70 the compound 1037 was replaced by compound 1013 to obtain the compound 1015.

Yield: 0.98 g (yield: 47.2%)

EXAMPLE 72

3-ethyl-6-[4-(N-cyclohexyl-N-methyl-aminocarbonyl) butoxy]-2-oxo-1,2-dihydroquinoxaline (compound 1014):

Compound 1013 (5.0 mM) was added to tetrahydrofuran 20 ml. An equimolar amount of triethylamine was added thereto, and there was further added dropwise an equimolar amount of chloroisobutyl formate at −10° C. and the mixture was stirred at −10° C. for 1 hour. N-methylcyclohexylamine 0.68 ml was added at one, and the mixture was stirred for 3 hours while gradually adjusting its temperature to room temperature. Chloroform was added to the reaction mixture, and the mixture was washed with dilute aqueous potassium carbonate. The aqueous layer was further extracted with chloroform. The combined chloroform layers were dried by adding anhydrous sodium sulfate and concentrated in vacuo. The residue was charged on a column of silica gel (C-200, 120 g) and eluted with chloroform-methanol (50:1) to obtain the compound 1014.

Yield: 1.41 g (yield: 73.2%)

EXAMPLE 73

3-ethyl-6-[4-(N-cyclohexyl-N-methyl-aminocarbonyl) butoxy]-2-oxo-1,2-dihydroquinoxaline (compound 1035):

In Example 72 the compound 1013 was replaced by compound 1037 and N-methylcyclohexylamine was replaced by N-ethylcyclohexylamine 0.77 ml to obtain the compound 1035.

Yield: 1.49 g (yield: 77.4%)

TABLE 3

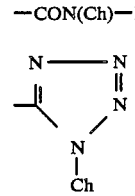

| Comp. No. | Z | — | $R_1$ | A | R |
|---|---|---|---|---|---|
| 896 | N | = | H | —(CH$_2$)$_3$— | —CON(Ch)—Me |
| 913 | N | = | H | —(CH$_2$)$_4$— | 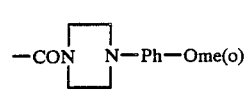 |
| 914 | N | = | H |  —(CH$_2$)$_3$— | COOEt |
| 915 | N | = | H | " | —CON(Ch)—Et |
| 916 | N | = | H | " | —CON(Ch)—CH$_2$Ph |
| 917 | N | = | H | " | —CON(Ch)—CH$_2$—CH$_2$OH |
| 918 | N | = | H | " | 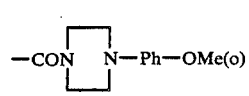 |
| 919 | N | = | H | —(CH$_2$)$_4$ | —COOEt |
| 920 | N | = | H | " | —CON(Ch)—Me |
| 921 | N | = | H | " | —CON(Ch)—Et |
| 922 | N | = | H | " | —CON(Ch)—CH$_2$Ph |
| 923 | N | = | H | " | —CON(Ch)—CH$_2$CH$_2$OH |
| 924 | N | = | H | " | —CON N—Ph—OMe(o) |
| 925 | NH | — | H | —(CH$_2$)$_3$— | —COOH |
| 927 | NH | — | H | —(CH$_2$)$_4$— | " |
| 929 | NH | — | H | —(CH$_2$)$_3$— | —CON(Ch)—Me |
| 931 | NH | — | H | —(CH$_2$)$_4$— | 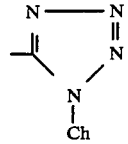 |

TABLE 3-continued $$\text{R}_1\text{-C(Z)=... O-A-R structure with NH and C=O}$$

| Comp. No. | Z | — | R₁ | A | R |
|---|---|---|---|---|---|
| 938 | N | = | H | —(CH₂)₃— | —COOH |
| 945 | N | = | Me | " | —COOEt |
| 946 | N | = | Et | " | " |
| 947 | N | = | Pro | " | " |
| 948 | N | = | Bu | " | " |
| 949 | N | = | —(CH₂)₅CH₃ | " | " |
| 950 | N | = | —(CH₂)₈CH₃ | " | " |
| 951 | N | = | —(CH₂)₁₁CH₃ | " | " |
| 952 | N | = | —(CH₂)₁₃CH₃ | " | " |
| 953 | N | = | —(CH₂)₁₅CH₃ | " | " |
| 954 | N | = | Ph | " | " |
| 955 | N | = | Me | " | —COOH |
| 956 | N | = | Et | " | " |
| 957 | N | = | Pro | " | " |
| 958 | N | = | Bu | " | " |
| 959 | N | = | —(CH₂)₅CH₃ | " | " |
| 960 | N | = | —(CH₂)₈CH₃ | " | " |
| 961 | N | = | —(CH₂)₁₁CH₃ | —(CH₂)₃— | —COOH |
| 962 | N | = | —(CH₂)₁₃CH₃ | " | " |
| 963 | N | = | —(CH₂)₁₅CH₃ | " | " |
| 964 | N | = | Ph | " | |
| 965 | N | = | Me | " | —CON(Ch)—Me |
| 966 | N | = | Me | " | —CON(Ch)—CH₂CH₂OH |
| 967 | N | = | Me | " | —CONEt₂ |
| 968 | N | = | Me | " | —CON⌐N—Ph—Ome(o) |
| 969 | N | = | Me | " | —CON(Ch)—CH₂Ph |
| 970 | N | = | Me | " | —CON⌐CH—Ph |
| 971 | N | = | Et | " | —CON(Ch)—Me |
| 972 | N | = | Et | " | —CON(Ch)—CH₂CH₂OH |
| 973 | N | = | Et | " | —CON⌐N—Ph—Ome(o) |
| 974 | N | = | Pro | " | —CON(Ch)—Me |
| 975 | N | = | Pro | " | —CON(Ch)—CH₂CH₂OH |
| 976 | N | = | Bu | " | —CON(Ch)—Me |
| 977 | N | = | —(CH₂)₅CH₃ | " | —CON(Ch)—Me |
| 978 | N | = | " | " | —CON(Ch)—CH₂CH₂OH |
| 979 | N | = | —(CH₂)₈CH₃ | " | —CON(Ch)—Me |
| 980 | N | = | —(CH₂)₁₁CH₃ | " | —CON(Ch)—Me |
| 981 | N | = | —(CH₂)₁₁CH₃ | —(CH₂)₃— | —CON(Ch)—CH₂CH₂OH |
| 982 | N | = | —(CH₂)₁₃CH₃ | " | —CON(Ch)—Me |
| 983 | N | = | " | " | —CON(Ch)—CH₂CH₂OH |
| 984 | N | = | —(CH₂)₁₅CH₃ | " | —CON(Ch)—Me |
| 985 | N | = | " | " | —CON(Ch)—CH₂CH₂OH |
| 986 | N | = | Ph | " | —CON(Ch)—Me |
| 987 | N | = | Ph | " | —CON(Ch)—CH₂CH₂OH |
| 988 | N | = | Ph | " | —CONEt₂ |
| 989 | N | = | Ph | " | —CON(Ch)—Me |
| 990 | N | = | Ph | " | —CON⌐N—Ph—OMe(o) |
| 991 | N | = | Ph | " | —CON⌐CH—Ph |
| 1012 | N | = | Et | —(CH₂)₄ | —COOET |

TABLE 3-continued

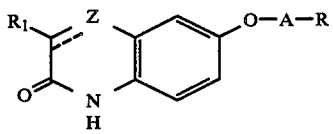

| Comp. No. | Z | — | R₁ | A | R |
|---|---|---|---|---|---|
| 1013 | N | = | Et | " | —COOH |
| 1014 | N | = | Et | " | —CON(Ch)Me |
| 1015 | N | = | Et | " | —CON(Ch)CH₂CH₂OH |
| 1029 | N | = | Me | —(CH₂)₃— | —CON(Ch)Et |
| 1034 | N | = | Me | —(CH₂)₄— | —CON(Ch)CH₂CH₂OH |
| 1035 | N | = | Me | " | —CON(Ch)Et |
| 1036 | N | = | Me | " | —COOEt |
| 1037 | N | = | Me | " | —COOH |

Me;methyl
Et;ethyl
Pro;propyl
Bu;butyl
Ph;benzene ring
Ch;cyclohexane ring

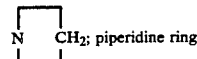 ; piperidine ring

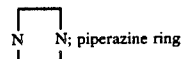 ; piperazine ring ( ) position of substituent

TABLE 4

N—(5-hydroxy-2-nitrophenyl)-amino acid ethyl ester

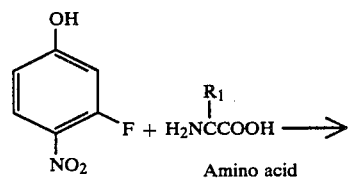
Phenol    Amino acid

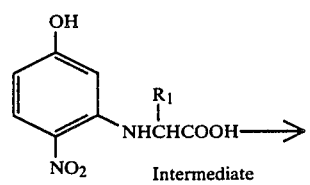
Intermediate

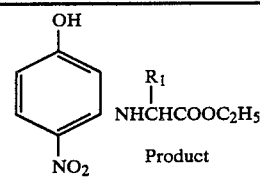
Product

| Ref. Ex. | Reaction Scale | Amino acid (R₁) | Reflux time (day) | Product Yield (g) | Yield (%) |
|---|---|---|---|---|---|
| 1 | 90 mM | —CH₃ | 5 | 20.43 | 89.4 |
| 2 | 60 mM | —CH₂CH₃ | 5 | 13.21 | 86.7 |
| 3 | 30 mM | —(CH₂)₂CH₃ | 3 | 7.56 | 89.4 |
| 4 | 30 mM | —(CH₂)₃CH₃ | 6 | 8.59 | 96.7 |
| 5 | 30 mM | —(CH₂)₅CH₃ | 3 | 9.16 | 94.2 |
| 6 | 30 mM | —(CH₂)₈CH₃ | 5 | 8.94 | 81.4 |
| 7 | 30 mM | —(CH₂)₁₁CH₃ | 4 | 12.91 | 100 |
| 8 | 30 mM | —(CH₂)₁₃CH₃ | 5 | 12.05 | 92.1 |
| 9 | 36 mM | —(CH₂)₁₅CH₃ | 8 | 14.05 | 84.1 |
| 10 | 30 mM | phenyl | 3 | 9.10 | 96.0 |

TABLE 5

Physical properties of N—(5-hydroxy-2-nitrophenyl)-amino acid ethyl ester

| Ref Ex. | N.M.R. $\delta_{CDCl_3}^{TMS}$ P.P.M. | Mass (CI) |
|---|---|---|
| 1 | 1.29(3H, t, J = 7), 1.60(3H, d, J = 7), 4.25(2H, q, J = 6), 6.07(1H, d, J = 2.5), 6.19(1H, d.d, J = 2.5, 10), 6.47(1H, s), 8.12(2H, d, J = 10), 8.44(1H, b.d, J = 7) | 255<br>181 |
| 2 | 1.05(3H, t, J = 7), 1.29(3H, t, J = 7), 1.8~2.2(2H, m), 3.9~4.3(1H, m), 4.25(2H, q, J = 8), 6.10(1H, d, J = 2.5), 6.20(1H, d.d, J = 2.5, 10), 7.4(1H, b.s), 8.09(1H, d, J = 10), 8.57(1H, d, J = 7) | 269<br>195 |
| 3 | 0.97(3H, t, J = 7), 1.28(3H, t, J = 7), 1.5~1.7(2H, m), 1.7~2.1(2H, m), 3.9~4.3(1H, m), 4.27(2H, q, J = 7), 6.08(1H, d, J = 2.5), 6.21(1H, d.d, J = 2.5, 10), 7.1(1H, b.s), 8.08(1H, d, J = 10), 8.50(1H, d, J = 7) | 283<br>209 |
| 4 | 0.92(3H, t, J = 7), 1.28(3H, t, J = 7), 1.2~1.6(4H, m), 1.7~2.1(2H, m), 3.9~4.3(1H, m), 4.24(2H, q, J = 7), 6.09(1H, d, J = 2.5, 10), 6.19(1H, d.d, J = 2.5, 10), 8.09(1H, d, J = 10)8.52(1H, d, J = 7) | 297<br>223 |
| 5 | 0.87(3H, t, J = 7), 1.28(3H, t, J = 7), 1.2~1.6(8H, m), 1.7~2.1(2H, m), 3.9~4.3(1H, m), 4.23(2H, q, J = 7), 6.08 | 325<br>251 |

TABLE 5-continued

Physical properties of N—(5-hydroxy-2-nitrophenyl)-amino acid ethyl ester

| Ref Ex. | N.M.R. $\delta_{CDCl_3}^{TMS}$ P.P.M. | Mass (CI) |
|---|---|---|
|  | (1H, d, J = 2.5), 6.19(1H, d.d, J = 2.5, 10), 8.10((1H, d, J = 10), 8.50(1H, d, J = 7) | |
| 6 | 0.87(3h, t, J = 7), 1.0~1.7 (14H, m), 1.27(3H, d, J = 7), 1.7~2.1(2H, m), 3.9~4.3(1H, m), 4.24(2H, q, J = 8), 6.11(1H, d, J = 2.5), 6.18(1H, d.d, J = 2.5, 10), 8.10(1H, d, J = 10), 8.50(1H, d, J = 7) | 367 293 |
| 7 | 0.88(3H, t, J = 7), 1.1~1.6(20H, m), 1.27(3H, t, J = 7), 1.7~2.1(2H, m), 3.9~4.3(1H, m), 4.23(2H, q, J = 8), 6.08 (1H, d, J = 2.5), 6.17(1H, d.d, J = 2.5, 10), 8.11 ((1H, d J = 10), 8.49(1H, d, J = 7) | 409 335 |
| 8 | 0.88(3H, t, J = 7), 1.27(3H, t, J = 7), 1.1~1.6(2H, m), 1.7~2.1(2H, m), 3.9~4.2(1H, m), 3.9~4.23(2H, q, J = 7), 6.07(1H, d, J = 2.5), 6.18(1H, d.d, J = 2.5, 10), 6.5(1H, bs), 8.18(1H, d, J = 10), 8.48 (1H, d, J = 7) | 437 363 |
| 9 | 0.88(3H, t, J = 7), 1.27(3H, t, J = 7), 1.0~1.7(28H, m), 1.7~2.1(2H, m), 3.9~4.2(1H, m), 4.24(2H, q, J = 7), 6.08(1H, d, J = 2.5), 6.18(1H, d.d, J = 2.5, 10), 6.8 (1H, bs), 8.10(1H, d, J = 10), 8.51(1H, D, J = 7) | 465 391 |
| 10 | 1.22(3H, t, J = 7), 4.21(2H, q, J = 7), 5.14(1H, d, J = 7), 5.92(1H, d, J = 2.5), 6.17(1H, d.d, J = 2.5, 10), 7.2~7.6 5H, m), 8.12(1H, d, J = 10), 9.30(1H, d, J = 7) | 317 243 |

TABLE 6

N—[5-(3-ethoxycarbonyl)-propoxy-2-nitrophenyl]-amino acid ethyl ester

Starting material → Product

| Ref. Ex. | Reaction Scale mM | Heat time (hr.) | Silica gel (g) | $R_1$ | Product Yield (g) | Yield (%) |
|---|---|---|---|---|---|---|
| 11 | 45 (11.43 g) | 8 | 250 | —CH$_3$ | 14.02 | 84.7 |
| 12 | 21 (5.63 g) | 14 | 180 | —CH$_2$CH$_3$ | 6.73 | 83.9 |
| 13 | 25 (7.05 g) | 10 | 180 | —(CH$_2$)$_2$CH$_3$ | 9.06 | 91.5 |
| 14 | 20 (5.92 g) | 6 | 170 | —(CH$_2$)$_3$CH$_3$ | 6.62 | 80.7 |
| 15 | 17 (5.51 g) | 6 | 170 | —(CH$_2$)$_5$CH$_3$ | 6.48 | 87.0 |
| 16 | 20 (7.32 g) | 10 | 180 | —(CH$_2$)$_8$CH$_3$ | 8.32 | 86.7 |
| 17 | 26 (10.61 g) | 8 | 220 | —(CH$_2$)$_{11}$CH$_3$ | 11.82 | 87.1 |
| 18 | 27 (11.77 g) | 10 | 220 | —(CH$_2$)$_{13}$CH$_3$ | 12.78 | 86.1 |
| 19 | 22 (10.21 g) | 8 | 220 | —(CH$_2$)$_{15}$CH$_3$ | 10.37 | 81.6 |
| 20 | 30 (9.38 g) | 10 | 220 | phenyl | 10.95 | 84.9 |

TABLE 7

Physical properties of N—[5-(3-ethoxycarbonyl)-propoxy-2-nitrophenyl] amino acid ethyl ester

| Ref. Ex. | N.M.R. $\delta_{CDCl_3}^{TMS}$P.P.M. | Mass (CI) |
|---|---|---|
| 11 | 1.27 (3H, t, J = 7), 1.29 (3H, t, J = 7), 1.60 (3H, d, J = 7), 2.14 (2H, q, J = 7), 2.47 (2H, t, J = 7), 3.9~4.4 (7H, m), 6.06 (1H, d, J = 2.5), 6.25 (1H, d, J = 2.5, 10), 8.15 (1H, d.d, J = 10), 8.53 (1H, d, J = 7) | 369 295 253 115 |
| 12 | 1.05 (3H, t, J = 7), 1.27 (3H, t, J = 7), 1.28 (3H, t, J = 7), 1.7~2.3 (4H, m), 2.50 (2H, t, J = 7), 3.9~4.4 (7H, m) 6.07 (1H, d, J = 2.5), 6.25 (1H, d.d, J = 2.5, 10), 8.15 (1H,d, J = 10), 8.54 (1H, d, J = 7) | 383 309 297 115 |
| 13 | 0.98 (3H, t, J = 7), 1.27 (3H × 2, t, J = 7), 1.3~3.3 (8H, m), 2.50 (2H, t, J = 7), 3.9~4.4 (7H, m), 6.07 (1H, d, J = 2.5), 6.24 (1H, d.d, J=2.5, 10), 8.15 (1H, d, J = 10), 8.52 (1H, d, J = 7) | 397 323 115 |
| 14 | 0.92 (3H, t, J = 7), 1.27 (3H × 2, t, J = 7), 1.3~2.3 (10H, m), 2.50 (2H, t, J = 7), 3.9~4.4 (7H, m), 6.07 (1H, d, J = 2.5), 6.25 (1H, d.d, J = 2.5, 10), 8.15 (1H, d, J = 10), 8.52 (1H, d, J = 7) | 411 337 115 |
| 15 | 0.88 (3H, t, J = 7), 1.26 (3H × 2, t, J = 7), 1.2~2.3 (14H, m), 2.50 (2H, t, J = 7), 3.9~4.4 (7H, m), 6.07 (1H, d, J = 2.5), 6.24 (1H, d.d, J = 2.5, 10), 8.15 (1H, d, J = 10), 8.52 (1H, d, J = 7) | 439 365 253 115 |
| 16 | 0.88 (3H, t, J = 7), 1.27 (3H × 2, t, J = 7), 1.3~2.3 (20H, m), 2.50 (2H, t, J = 7), 3.9~4.4 (7H, m), 6.06 (1H, d, J = 2.5), 6.25 (1H, d.d, J = 2.5, 10), 8.15 (1H, d, J = 10), 8.52 (1H, d, J = 7) | 481 407 115 |

TABLE 7-continued

Physical properties of N—[5-(3-ethoxycarbonyl)-propoxy-2-nitrophenyl] amino acid ethyl ester

| Ref. Ex. | N.M.R. $\delta^{TMS}_{CDCl_3}$ P.P.M. | Mass (CI) |
|---|---|---|
| 17 | 0.88 (3H, t, J = 7), 1.26 (3H × 2, t, J = 7), 1.3~2.3 (26H, m), 2.50 (2H, t, J = 7), 3.9~4.4 (7H, m), 6.07 (1H, d, J = 2.5), 6.25 (1H, d.d, J = 2.5, 10), 8.15 (1H, d, J = 10), 8.52 (1H, d, J = 7) | 523<br>449<br>253<br>115 |
| 18 | 0.88 (3H, t, J = 7), 1.26 (3H × 2, t, J = 7), 1.3~2.3 (30H, m), 2.50 (2H, t, J = 7), 3.9~4.4 (7H, m), 6.07 (1H, d, J = 2.5), 6.25 (1H, d, J = 2.5, 10), 8.15 (1H, d, J = 10), 8.52 (1H, d, J = 7) | 551<br>477<br>251<br>115 |
| 19 | 0.88 (3H, t, J = 7), 1.25 (3H × 2, t, J = 7), 1.3~2.3 (34H, m), 2.50 (2H, t, J = 7), 3.9~4.4 (7H, m), 6.07 (1H, d, J = 2.5), 6.25 (1H, d, J = 2.5, 10), 8.15 (1H, d, J = 10), 8.52 (1H, d, J = 7) | 579<br>505<br>253<br>115 |
| 20 | 1.23 (3H, t, J = 7), 1.25 (3H, t, J = 7), 2.00 (2H, q, J = 7), 2.42 (2H, t, J = 7), 3.6~4.4 (6H, m), 5.17 (1H, d, J = 7), 5.89 (1H, d, J = 3), 6.20 (1H, d.d, J = 10), 7.2~7.6 (5H, m), 8.15 (1H, d, J = 10), 9.33 (1H, d, J = 7) | 431<br>357<br>115 |

TABLE 8

3-substituted-6-(3-ethoxycarbonyl propoxy)-2-oxo-1,2-dihydroquinoxaline

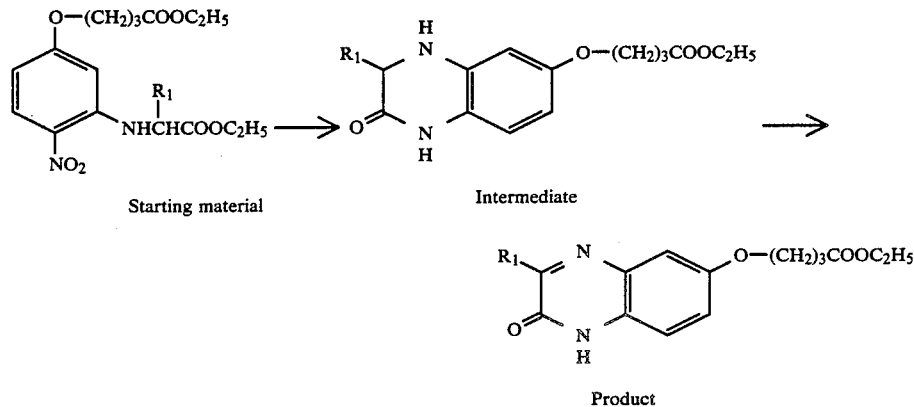

| Examp. | Starting material | Ethanol (ml) | Iron powder (g) | HCl (ml) | DDQ (g) | Silica gel (g) | Product Comp. No. | Yield (g) | Yield (%) |
|---|---|---|---|---|---|---|---|---|---|
| 1 | 33.3 | 200 | 9.3 | 70 | 7.56 | 240 | 945 | 6.20 | 64.3 |
| 2 | 27.4 | 200 | 7.7 | 50 | 6.22 | 240 | 946 | 5.96 | 71.5 |
| 3 | 14.6 | 100 | 4.1 | 30 | 3.31 | 120 | 947 | 2.42 | 52.1 |
| 4 | 12.1 | 100 | 3.4 | 25 | 2.75 | 120 | 948 | 2.43 | 60.4 |
| 5 | 14.8 | 100 | 4.1 | 30 | 3.36 | 170 | 949 | 3.56 | 66.8 |
| 6 | 5.67 | 70 | 1.6 | 12 | 1.29 | 80 | 950 | 1.22 | 63.0 |
| 7 | 14.4 | 100 | 4.1 | 30 | 3.27 | 170 | 951 | 3.84 | 60.0 |
| 8 | 7.5 | 70 | 2.1 | 15 | 1.70 | 120 | 952 | 2.32 | 65.5 |
| 9 | 8.5 | 100 | 2.4 | 20 | 1.93 | 120 | 953 | 2.64 | 62.1 |
| 10 | 23.6 | 200 | 6.6 | 50 | 5.36 | 240 | 954 | 6.80 | 81.8 |

TABLE 9

3-substituted-6-(3-carboxypropoxy)-2-oxo-1,2-dihydroquinoxaline

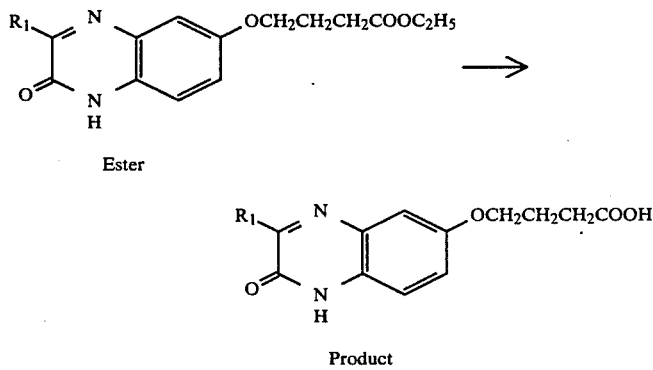

TABLE 9-continued

| | Ester | | | Product | | |
|---|---|---|---|---|---|---|
| Example | Compound No. | Amount used (g) | (mM) | 2N—NaOH (ml) | Compound No. | Yield (g) | Yield (%) |
| 11 | 945 | 5.70 | 19.66 | 20 | 955 | 5.05 | 98.0 |
| 12 | 946 | 5.48 | 18.03 | 18 | 956 | 4.88 | 98.1 |
| 13 | 947 | 2.20 | 6.92 | 7 | 957 | 1.86 | 92.0 |
| 14 | 948 | 2.14 | 6.45 | 7 | 958 | 1.81 | 92.3 |
| 15 | 949 | 3.28 | 9.11 | 9 | 959 | 2.80 | 92.6 |
| 16 | 950 | 1.18 | 2.94 | 3 | 960 | 1.12 | 98.9 |
| 17 | 951 | 3.44 | 7.75 | 8 | 961 | 3.20 | 100 |
| 18 | 952 | 2.08 | 4.41 | 5 | 962 | 1.89 | 96.0 |
| 19 | 953 | 2.32 | 4.64 | 5 | 963 | 2.05 | 93.0 |
| 20 | 954 | 6.20 | 17.95 | 18 | 964 | 5.61 | 98.6 |

TABLE 10

3-substituted-6-[N,N—di-substituted-aminocarbonyl)-propoxy]-2-oxo-1,2-dihydroquinoxaline

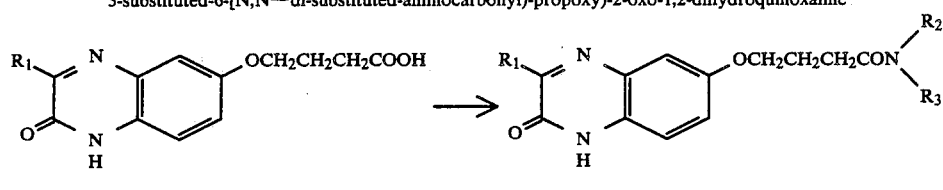

Carboxylic acid → Product

| Example | Carboxylic acid Compound No. | Used mM | Amine HN(R_2)(R_3) | Used | chloroform:methanol | Product Compound No. | Yield (g) | Yield (%) |
|---|---|---|---|---|---|---|---|---|
| 21 | 955 | 2.0 | HN(Ch)—Me | 0.27 ml | 50:1 | 965 | 0.44 | 61.6 |
| 22 | 955 | 2.0 | HN(Ch)—CH$_2$CH$_2$OH | 0.29 g | 30:1 | 966 | 0.29 | 37.5 |
| 23 | 955 | 2.0 | HNEt$_2$ | 0.15 g | 50:1 | 967 | 0.47 | 74.1 |
| 24 | 955 | 2.0 | HN⌐⌐N—Ph—OMe | 0.39 g | 70:1 | 968 | 0.44 | 50.5 |
| 25 | 955 | 2.0 | HN(Ch)—CH$_2$Ph | 0.38 g | 70:1 | 969 | 0.60 | 69.3 |
| 26 | 955 | 2.0 | HN⌐⌐CH—Ph | 0.33 g | 100:1 | 970 | 0.54 | 66.7 |
| 27 | 956 | 2.0 | HN(Ch)—Me | 0.27 ml | 200:1 | 971 | 0.37 | 49.9 |
| 28 | 956 | 2.0 | HN(Ch)—CH$_2$CH$_2$OH | 0.29 g | 50:1 | 972 | 0.43 | 53.6 |
| 29 | 956 | 2.0 | HN⌐⌐N—Ph—OMe(o) | 0.39 g | 200:1 | 973 | 0.76 | 59.2 |
| 30 | 957 | 2.0 | HN(Ch)—Me | 0.27 ml | 200:1 | 974 | 0.61 | 79.2 |
| 31 | 957 | 2.0 | HN(Ch)—CH$_2$CH$_2$OH | 0.29 g | 20:1 | 975 | 0.03 | 14.4 |
| 32 | 958 | 1.0 | HN(Ch)—Me | 0.145 ml | 200:1 | 976 | 0.28 | 70.2 |
| 33 | 959 | 2.0 | " | 0.27 ml | 200:1 | 977 | 0.50 | 58.5 |
| 34 | 959 | 2.0 | HN(Ch)—CH$_2$CH$_2$OH | 0.29 g | 50:1 | 978 | 0.44 | 48.1 |
| 35 | 960 | 1.5 | HN(Ch)—Me | 0.21 ml | 200:1 | 979 | 0.52 | 73.9 |
| 36 | 961 | 1.5 | " | 0.21 ml | 200:1 | 980 | 0.48 | 62.6 |
| 37 | 961 | 1.5 | HN(Ch)—CH$_2$CH$_2$OH | 0.22 ml | 50:1 | 981 | 0.26 | 62.0 |
| 38 | 962 | 1.5 | HN(Ch)—Me | 0.21 ml | 200:1 | 982 | 0.27 | 33.4 |
| 39 | 962 | 1.5 | HN(Ch)—CH$_2$CH$_2$OH | 0.22 g | 50:1 | 983 | 0.28 | 32.8 |
| 40 | 963 | 1.35 | HN(Ch)—Me | 0.19 ml | 200:1 | 984 | 0.53 | 69.2 |
| 41 | 963 | 1.35 | HN(Ch)—CH$_2$CH$_2$OH | 0.20 | 50:1 | 985 | 0.37 | 39.1 |
| 42 | 964 | 2.0 | HN(Ch)—Me | 0.27 ml | 100:1 | 986 | 0.43 | 51.3 |
| 43 | 964 | 2.0 | HN(Ch)—CH$_2$CH$_2$OH | 0.22 g | 30:1 | 987 | 0.50 | 55.7 |
| 44 | 964 | 2.0 | HNEt$_2$ | 0.15 g | 100:1 | 988 | 0.39 | 51.5 |
| 45 | 964 | 2.0 | HN(CH)—CH$_2$Ph | 0.38 g | 100:1 | 989 | 0.64 | 64.6 |

TABLE 10-continued

| | | | | | | | | |
|---|---|---|---|---|---|---|---|---|
| 46 | 964 | 2.0 | 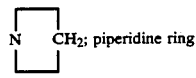 HN̄ N—Ph—OMe(o) | 0.39 g | 100:1 | 990 | 0.62 | 62.2 |
| 47 | 964 | 2.0 | 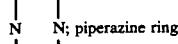 HN̄ CH—Ph | 0.33 g | 100:1 | 991 | 0.72 | 77.1 |

Me; methyl
Et; ethyl
Pro; propyl
Bu; butyl
Ph; benzene ring
Ch; cyclohexane ring N̄ CH$_2$; piperidine ring N̄ N; piperazine ring ( ) position of substituent

TABLE 11

6-(N,N—di-substituted-aminocarbonyl)-alkoxy-2-oxo-1,2-dihydroquinoxaline $$\underset{\underset{H}{N}}{\overset{N}{\bigcirc}} \!\!\!\! \begin{array}{c} \\ \end{array} \!\!\!\! O-(CH_2)_n COOC_2H_5H_5 \longrightarrow$$

$$\underset{\underset{H}{N}}{\overset{N}{\bigcirc}} \!\!\!\! \begin{array}{c} \\ \end{array} \!\!\!\! O-(CH_2)_n COOH \longrightarrow$$

$$\underset{\underset{H}{N}}{\overset{N}{\bigcirc}} \!\!\!\! \begin{array}{c} \\ \end{array} \!\!\!\! O-(CH_2)_n COOH$$

| | | | Amine HR⟨R$_2$/R$_3$⟩ | | Product | |
|---|---|---|---|---|---|---|
| Example | Starting Comp. No. | n | R$_3$ | Comp. No. | Yield (mg) | Yield (%) |
| 50 | 914 | 3 | HN(Ch)—Me | 896 | 780 | 63 |
| 51 | 914 | 3 | HN(Ch)—Et | 915 | 770 | 51 |
| 52 | 914 | 3 | HN(Ch)—CH$_2$Ph | 916 | 750 | 50 |
| 53 | 914 | 3 | HN(Ch)—CH$_2$CH$_2$OH | 917 | 850 | 63 |
| 54 | 914 | 3 | 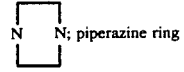 HN̄ N—Ph—OMe(o) | 918 | 656 | 43 |
| 57 | 919 | 4 | HN(Ch)—Me | 920 | 775 | 60 |
| 58 | 919 | .4 | HN(Ch)—Et | 921 | 607 | 45 |
| 59 | 919 | 4 | HN(Ch)—CH$_2$Ph | 922 | 377 | 24 |
| 60 | 919 | 4 | HN(Ch)—CH$_2$CH$_2$OH | 923 | 879 | 63 |
| 61 | 919 | 4 | HN̄ N—Ph—Pme(o) | 924 | 544 | 35 |

Me; methyl
Et; ethyl
Ch; cyclohexane ring
Ph; benzene ring

N̄ N; piperazine ring ( ) position of substituent

TABLE 12

| Comp. No. | N. M. R. $\delta_{CDCl_3}^{TMS}$ P. P. M. | Mass (CI) | TLC |
|---|---|---|---|
| 896 | 1.0~2.0(m, 12 H, 6CH$_2$), 2.19(q, 2H, CH$_2$), 2.53 (t, 2H, CH$_2$), 2.83, 2.85(each s, 3H, CH$_3$), 4.12 (t, 2H, CH$_2$), 3.3~3.7, 4.1~4.7(each b, 1H, CH), 7.2~7.4 (m, 3H, phenyl proton), 8.34 (s, 1H, CH), 12.7 (b. s, 1H, NH) | 344 | Rfb = 0.43 |
| 913 | 1.0~2.4 (m, 14H, 7CH$_2$), 2.94 (t, 2H, CH$_2$), 4.10 (t, 2H, CH$_2$), 3.9~4.3 9m, 1H, CH), 7.0~7.4 (m, 3, phenyl proton), 8.35 9s, 1H, CH), 12.74 (b. s, 1H, NH) | 369 (M$^+$ + 1) | Rfb = 0.29 |
| 915 | 1.20 9t, 3H, CH$_3$), 1.9~2.0 (m, 10H, 5CH$_2$), 2.20 (q, 2H, CH$_2$), 2.57 (t, 2H, CH$_2$), 3.1~3.5 (m, 2H, CH$_2$), 4.11 (t, 2H, CH$_2$), 3.4~3.8, 4.1~4.5 (m, 1H, CH), 7.0~7.5 (m, 3H, phenyl proton), 8.33 9s, 1H, CH) | 358 (M$^+$ + 1) | Rfb = 0.51 |
| 916 | 0.8~2.0 (m, 10H, 5CH$_2$), 1.9~2.7 (m, 4H, 2CH$_2$), 3.5~3.9, 4.1~4.5 (m, 1H, CH), 4.03 (t, 2H, CH$_2$), 4.55 (d, 2H, CH$_2$) 7.0~7.4 (m, 8H, phenyl proton), 8.34 (s, 1H, CH) | 420 (M$^+$ + 1) | Rfb = 0.54 |
| 917 | 1.0~2.0 (m, 10H, 5CH$_2$), 2.20 (q, 2H, CH$_2$), 2.63 (t, 2H, CH$_2$), 3.4~3.8 (m, 4H, 2CH$_2$), 4.12 (t, 2H, CH$_2$), 7.1~7.4 (m, 3H, phenyl proton), 8.32 (s, 1H, CH) | 374 (M$^+$ + 1) | Rfb = 0.42 |
| 918 | 2.22 (q, 2H, CH$_2$), 2.62 (t, 2H, CH$_2$), 2.9~3.2 (m, 4H, 2 CH$_2$), 3.6~4.0 (m, 4H, 2CH$_2$), 3.88 (s, 3H, CH$_3$), 4.13 (t, 2H, CH$_2$), 6.8~7.2 (m, 4H, phenyl proton), 8.34 (s, 1H, CH) CH), 12.6 (b. s. 1H, NH) | 423 (M$^+$ + 1) | Rfb = 0.51 |
| 919 | 1.26 (t, 3H, CH$_3$), 1.7~2.0 (m, 4H, 2CH$_2$), 2.41 (t, 2H, CH$_2$), 4.05 (t, 2H, CH$_2$), 4.14 (q, 2H, CH$_2$), 7.2~7.4 (m, 3H, phenyl proton), 8.35 (s, 1H, CH), 12.55 (b. s, 1H, NH) | 346 (M$^+$ + 1) | Rfb = 0.52 |
| 920 | 0.9~2.1 (m, 14H, 7CH$_2$), 2.42 (t, 2H, CH$_2$), 2.85 (s, 3H, CH$_3$), 3.3~3.8, 4.2~4.7 (m, 1H, CH), 4.05 (t, 2H, CH$_2$), 7.0~7.5 (m, 3H, phenyl proton), 8.32 (s, 1H, CH) | 358 (M$^+$ + 1) | Rfb = 0.52 |
| 921 | 0.8~2.2 (m, 14h, 7CH$_3$), 1.19 (t, 3H, CH$_3$), 2.42 (t, 3H, CH$_2$), 3.1~3.5 (m, 2H, CH$_2$), 3.3~3.8, 4.1~4.5 (m, 1H, CH), 4.06 (t, 2HG, CH$_2$), 7.0~7.5 (m, 3H, phenyl proton), 8.33 (s, 1H, CH), 12.97 (b. s, 1H, NH) | 734 (M$^+$ + 1) | Rfb = 0.56 |
| 922 | 0.8~2.0 (m, 14H, 7CH$_2$), 2.0~2.6 (m, 2H, CH$_2$), 3.4~3.8, 4.2~4.6 (m, 1H, CH), 3.7~4.1 (m, 2H, CH$_2$), 4.46 (d, 2H, CH$_2$), 6.8~7.3 (m, 8H, phenyl proton), 8.24 (s, 1H, CH), 12.88 (b. s, 1H, NH) | 434 (M$^+$ + 1) | Rfb = 0.56 |
| 923 | 0.8~1.3 (m, 14H, 7CH$_2$), 2.51 (t, 2H, CH$_2$), 3.2~3.9 (m, 4H, 2CH$_2$), 4.05 (t, 2H, CH$_2$), 3.2~4.5 (m, 1H, CH), 6.9~7.5 (m, 3H, phenyl proton), 8.32 (s, 1H, CH) | 388 (M$^+$ + 1) | Rfb = 0.43 |
| 924 | 1.7~2.1 (m, 4H, 2CH$_2$), 2.3~2.6 (m, 2H, CH$_2$), 2.9~3.2 (m, 4H, 2CH$_2$), 3.5~3.9 (m, 4H, 2CH$_2$), 3.87 (s, 3H, CH$_3$), 4.07 (t, 2H, CH$_2$), 6.7~7.5 (m, 7H, phenyl proton), 8.33 (s, 1 H, CH), 12.99 (b. s, 1H, NH) | 437 (M$^+$ + 1) | Rfb = 0.48 |
| 925 | 1.26 (t, 3H, CH$_3$), 2.07 (q, 2H, CH$_3$), 2.49 ((t, 2H, CH$_2$), 3.93 (t, 2H, CH$_2$), 3.96 (s, 2H, CH$_2$), 4.14 (q, 2H, CH$_2$), 6.2~6.3 (m, 2H, phenyl proton), 6.5~6.8 (m, 1H, phenyl proton, 8.65 (b. s, 1H, NH) | 279 (M$^+$ + 1) | Rfb = 0.61 |
| 927 | 1.25 (t, CH$_3$), 1.5~2.0 (m, 5H, CH$_2$, NH), 2.2~2.5 (m, 2H, CH$_2$), 3.67 (s, CH$_3$), 3.89 (t, 2H, CH$_2$), 3.95 (s, 2H, CH$_2$), 4.13 (q, 2H, CH$_2$), 6.1~6.4 (m, 2H, phenyl proton), 6.62 (d, 1h, phenyl proton), 8.27 (b. s, 1H, NH) | 293 (M$^+$ + 1) | Rfb = 0.59 |
| 929 | 0.9~2.0 (m, 10H, 5CH$_2$), 2.09 (q, 2H, CH$_2$), 2.47 (t, 2H, CH$_2$), 2.83 (s, 3H CH$_3$), 3.4~3.7, 4.2~4.6 (m, 1H, CH), 3.94 (s, 3H, CH$_3$), 3.8~4.2 (m, 2H CH$_2$), 6.1~6.4 (m, 1H, phenyl proton), 6.6~6.8 (m, 1H, phenyl proton), 9.44 (b. s, 1H, NH) | 346 (M$^+$ + 1) | Rfb = 0.58 |
| 931 | 1.1~2.4 (m, 14H, 7CH$_2$), 2.91 (t, 2H, CH$_2$), 3.96 (s, 2H, CH$_2$), 3.8~4.3 (m, 3H, CH$_2$, CH), 6.2~6.4 (m, 2H, phenyl proton), 6.6~6.7 (m, 1H, phenyl proton), 8.62 (b. s, 1H, NH) | 371 (M$^+$ + 1) | Rfb = 0.29 |
| 945 | 1.26 (3h, t, J=7), 2.19 (2H, q, J=8), 2.54 (2H, t, J=6), 2.63 (3H, s), 4.07 (1H, t, J=6), 4.15 (3H, d, J=7), 7.0~7.4 (3H, m), 11.6 (1H, b. s) | 291 115 | Rfa = 0.58 |
| 946 | 1.27 (3H, t, J=7), 1.31 (3H, t, J=7), 2.09 (2H, q, J=7), 2.54 (2H, t, J=7), 3.01 (2H, q, J=7), 4.09 (2H, t, J=7), 4.16 (2h, q, J=7), 7.0~7.4 (3H, m), 11.5 (1H, b. s) | 305 115 | Rfa = 0.63 |
| 948 | 1.08 (3H, t, J=7), 1.27 (3H, t, J=7), 1.4~2.2 (6H, m), 2.53 (2H, t, J=7), 2.99 (2H, t, J=7), 4.08 (2H, t, J=7), 4.16 (2H, q, J=7), 7.0~7.4 (3H, m), 11.3 (1H, b. s) | 333 115 | Rfa = 0.70 |
| 949 | 0.91 (3H, t, J=7), 1.27 (3H, t, j=7), 1.2~2.4 (10H, m), 2.54 (2H, t, J=7), 2.98 (2H, t, J=7), 4.08 (2H, t, J=7), 4.16 (2H, q, J=7), 7.0~7.4 (3H, m), 11.3 (1H, b. s) | 361 115 | Rfa = 0.74 |
| 950 | 0.87 (3H, t, J=7), 1.27 (3H, t, J=7), 1.2~2.4 (16H, m), 2.53 (2H, t, J=7), 2.98 (2H, t, J=7), 4.08 (2H, t, J=7), 4.16 (2H, q, J=7), 7.0~7.4 (3H, m), 11.8 (1H, b. s) | 403 290 115 | Rfa = 0.76 |
| 951 | 0.87 (3H, t, J=7), 1.27 (3H, t, J=7), 1.2~2.4 (22H, m), 2.54 (2H, t, J=7), 2.98 (2H, t, J=7), 4.08 (2H, t, J=7), 4.16 (2H, q, J=7), 7.0~7.4 (3H, m), 12.1 (1H, b. s) | 445 115 | Rfa = 0.79 |
| 952 | 0.88 (3H, t, J=7), 1.27 (3H, t, J=7), 1.2~2.4 (26H, m), 2.54 (2H, t, J=7), 2.97 (2H, t, J=&), 4.08 (2H, t, J=7), 4.16 (2H, q, J=7), 7.0~7.4 (3H, m), 11.8 (1H, b. s) | 473 115 | Rfa = 0.80 |

TABLE 12-continued

| Comp. No. | N. M. R. $\delta_{CDCl_3}^{TMS}$ P. P. M. | Mass (Cl) | TLC |
|---|---|---|---|
| 954 | 1.23 (3H, t, J=7), 2.17 (2H, q, J=7), 2.55 (2H, t, J=7), 4.10 (2H, t, J=7), 4.16 (2H, q, J=), 7.0~7.6 (6H, m), 8.3~8.5 (2H, m), 11.5 (1H, b. s) | 353 115 | Rfa = 0.71 |
| 965 | 1.0~2.0 (10H, m), 2.22 (2H, q, J=7), 2.53 (2H, t, J=7), 2.63 (3H, s), 2.85 (3H, m), 12.2 (1H, b) | 358 | Rfa = 0.51 |
| 966 | 1.0~2.0 (10H, m), 2.22 (2H, q, J=7), 2.54 (2H, t, J=7), 2.62 (3H, s), 3.4~4.6 (5H, m), 4.10 (2H, t, J=7), 7.0~7.4 (3H, m), 12.1 (1H, b) | 388 212 | Rfa = 0.26 |
| 967 | 1.17 (3H, t, J=7), 1.18 (3H, t, J=7), 2.23 (2H, q, J=7), 2.57 (2H, t, J=7), 2.63 (3H, s), 3.33 (2H, q, J=7), 3.40 (2H, q, J=7), 4.09 (2H, t, J=7), 7.0~7.4 (3H, m), 12.2 (1H, b) | 318 142 | Rfa = 0.40 |
| 968 | 2.25 (2H, q, J=7), 2.61 (3H, t, J=7), 2.62 (3H, s), 2.9~3.3 (4H, m), 3.7~3.9 (4H, M), 3.87 (3H, s), 4.11 (3H, t, J=7), 6.8~7.4 (7H, m), 12.3 (1H, b) | 437 251 | Rfa = 0.44 |
| 969 | 0.9~2.0 (10H, m), 2.21 (2H, q, J=7), 2.53 (2H, t, J=7), 2.63 (3H, s), 3.6~4.6 (1H, m), 4.14 (2H, t, J=7), 4.55 (2H, d, J=7), 6.8~7.4 (8H, m), 12.2 (1H, b) | 434 254 | Rfa = 0.53 |
| 970 | 1.4~2.1 (4H, m), 2.24 (2H, q, J=6), 2.4~3.4 (7H, m), 263 (3H, s), 4.12 (2H, t, J=7), 7.0~7.4 (8H, m), 12.5 (1H, b) | 406 230 | Rfa = 0.45 |
| 971 | 1.0~2.0 (13H, m, J=7), 1.37 (3H, t, J=7), 2.17 (2H, q, J=7), 2.53 (2H, t, J=7), 2.85 (3H, s) 3.01 (2H, q, J=7, 3.4~4.6 (1H, m), 4.11 (2H, t, J=7), 7.0~7.4 (3H, m), 12.2 (1H, b) | 372 182 | Rfa = 0.49 |
| 972 | 1.0~2.0 (10H, m), 1.36 (3H, t, J=7), 2.19 (2H, q, J=7), 2.59 (2H, t, J=7), 2.98 (2H, q, J=7), 3.4~4.6 (5H, m), 4.11 (2H, t, J=7), 7.0~7.4 (3H, m), 12.0 (1H, b) | 402 212 | Rfa = 0.25 |
| 973 | 1.36 (3H, t, J=7), 2.24 (2H, q, J=7), 2.62 (2H, t, J=7), 2.99 (2H, q, J=7), 2.9~3.2 (4H, m), 3.8~4.0 (4H, m), 3.88 (3H, s), 4.13 (2H, t, J=7), 6.8~7.4 (7H, m), 12.2 (1H, b) | 451 261 193 | Rfa = 0.46 |
| 974 | 1.07 (3H, t, J=7), 1.0~2.0 (12H, m), 2.22 (2H, q, J=7), 2.53 (2H, t, J=7), 2.85 (3H, s), 2.94 (2H, q, J=7), 3.4~4.6 (1H, m), 4.11 (2H, t, J=7), 7.0~7.4 (3H, m), 12.2 ((1H, b) | 386 182 | Rfa = 0.51 |
| 975 | 1.06 (3H, t, J=7), 1.0~2.4 (14H, m), 2.52 (2H, t, J=7), 2.95 (2H, q, J=7), 3.4~4.6 (1H, m), 4.12 ((2H, t, J=7), 7.0~7.4 (3H, m), 12.1 (1H, b), | 416 291 212 | Rfa = 0.25 |
| 976 | 0.99 (3H, t, J=7), 1.0~2.0 (14H, m), 2.20 (2H, q, J=7), 2 6.54 (2H, t, J=7), 2.85 (3H, s), 2.95 (2H, q, J=7), 3.4~4.6 91H, m), 4.11 (2H, t, J=7), 7.0~7.4 (3H, m), 12.1 (1H, b) | 400 182 | Rfa = 0.55 |
| 977 | 0.97 (3H, t, J=7), 1.0~2.0 (18H, m), 2.22 (2H, q, J=7), 2.53 (2H, t, J=7), 2.85 (3H, s), 2.92 (2H, q, J=7), 3.4~4.6 (1H, m), 4.11 (2H, t, J=7), 7.0~7.4 (3H, m), 12.1 (1H, b) | 428 182 | Rfa = 0.59 |
| 978 | 0.90 (3H, t, J=7), 1.0~2.0 (18 H, m), 2.21 (2H, q, J=7), 2.63 (2H, t, J=7), 2.95 (3H, t, J=7), 3.4~4.6 (5H, m), 4.11 (2H, t, J=7), 7.0~7.4 (3H, m), 12.1 (1H, b) | 458 347 247 212 | Rfa = 0.32 |
| 979 | 0.87 (3H, t, J=7), 1.0~2.0 (2H, m), 2.21 (2H, q, J=7), 2.51 (2H, t, J=7), 2.85 (3H, s), 2.92 (2H, q, J=7), 3.4~4.6 (1H, m), 4.11 (2H, t, J=7), 7.0~7.4 (3H, m), 12.1 (1H, b) | 470 279 182 | Rfa = 0.65 |
| 980 | 0.88 (3H, t, J=7), 1.0~2.0 (30H, M), 2.22 (2H, q, J=7), 2.52 (2H, t, J=7), 2.85 (3H, s), 2.95 (2H, t, J=7), 3.4~4.6 (1H, m), 4.11 (2H, t, J=7), 7.0~7.4 (3H, m), 12.1 (1H, b) | 512 331 182 114 | Rfa = 0.61 |
| 981 | 0.87 (3H, t, J=7), 1.0~2.0 (30H, m), 2.22 (2H, q, J=7), 3.52 (2H, t, J=7), 2.98 (2H, t, J=7), 3.4~4.6 (5H, m), 4.10 (2H, t, J=7), 7.0~7.4 (3H, m), 12.1 (1H, b) | 542 331 210 182 | Rfa = 0.38 |
| 982 | 0.87 (3H, t, J=7), 1.0~2.0 (34H, m), 2.22 (2H, q, J=7), 2.63 (2H, t, J=7), 2.85 (3H, s), 2.97 (2H, t, J=7), 3.4~4.6 (1H, m), 4.11 (2H, t, J=7), 7.0~7.4 (3H, m), 12.1 (1H, b) | 540 359 182 | Rfa = 0.72 |
| 983 | 0.87 (3H, t, J=7), 1.0~2.0 (38 H, m), 2.22 (2H, q, J=7), 2.63 (2H, t, J=7), 2.98 (2H, t, J=7), 3.4~4.6 (5H, m), 4.11 (2H, t, J=7), 7.0~7.4 (3H, m), 12.1 (1H, b) | 570 387 182 114 | Rfa = 0.43 |
| 984 | 0.87 (3H, t, J=7), 1.0~2.0 (42 H, m), 2.22 (2H, q, J=7), 2.58 (2H, t, J=7), 2.85 (3H, s), 2.97 (2H, t, J=7), 3.4~4.6 (1H, m), 4.10 (2H, t, J=7), 7.0~7.4 (3H, m), 12.1 (1H, b) | 568 473 325 182 | Rfa = 0.73 |
| 985 | 0.87 (3H, t, J=7), 1.0~2.0 (42 H, m), 2.21 (2H, q, J=7), 2.63 (2H, t, J=7), 2.95 (2H, t, J=7), 3.4~4.6 (5H, m), 4.11 (2H, t, J=7), 7.0~7.4 (3H, m), 12.1 (1H, b) | 598 459 | Rfa = 0.43 |
| 986 | 1.0~2.0 (10 H, m), 2.23 (2h, q, J=7), 2.56 (2H, t, J=7), 2.85 (2H, s), 3.4~4.6 (1H, m), 4.13 (2H, t, J=7), 7.0~7.6 (6H, m), 8.3~8.5 (2H, m), 12.5 (1H, b) | 420 182 | Rfa = 0.60 |
| 987 | 1.0~2.0 (10 H,m), 2.24 (2H, q, J=7), 2.64 (2H, t, J=7), 3.4~4.6 (5H, m), 4.11 (2H, t, J=7), 7.0~7.6 (6H, m), 8.2~8.6 (2H, m), 12.5 (1H, b) | 450 325 182 | Rfa = 0.42 |

TABLE 12-continued

| Comp. No. | N. M. R. $\delta_{CDCl_3}^{TMS}$ P. P. M. | Mass (CI) | TLC |
|---|---|---|---|
| 988 | 1.21 (3H × 2, t, J=7), 2.21 (2H, q, J=7), 2.56 (2H, t, J=7), 3.44 (2H × 2, q, J=7), 4.12 (2H, t, J=7), 7.0~7.6 (6H, m), 8.3~8.6 (2H, m), 12.5 91H, b) | 380 142 | Rfa = 0.56 |
| 989 | 0.8~2.0 (10H, m), 2.0~2.8 (4H, m), 3.7~3.9 (1H, m), 4.06 (2H, t, J=7), 4.55 (2H, d, J=7), 6.9~7.6 (11H, m), 8.3~8.5 (2H, m), 12.5 (1H, b) | 496 258 142 | Rfa = 0.75 |
| 990 | 2.22 (2H, q, J=7), 2.62 (2H, t, J=7), 2.9~3.2 (4H, m), 3.5~3.9 (4H, m), 3.86 (3H, s), 4.13 (2H, t, J=7), 6.8~7.6 (10H, m), 8.3~8.5 (2H, m), 12.8 (1H, b) | 499 453 239 192 | Rfa = 0.69 |
| 991 | 1.4~2.1 (4H, m), 2.23 (2H, q, J=7), 2.4~2.8 (7H, m), 4.14 (2H, , J=7), 7.0~7.6 (11H, m), 8.3~8.5 (2H, m), 12.6 (1H, b) | 463 239 162 | Rfa = 0.76 |
| 1012 | 1.26 (3H, t, J=7), 1.35 (3H, t, J=7), 1.6~2.0 (4H, m), 2.2~2.5 (2H,m), 3.02 (2H, q, J=7), 3.9~4.3 (4H, m), 7.0~7.4 (3H, m), 11.5 (1H, b) | | |
| 1013 | 1.24 (3H, t, J=7), 1.6~2.1 (4H, m), 2.42 (2H, t, J=7), 2.81 (2H, q, J=7), 4.03 (2H, t, J=7), 7.0~7.4 (3H, m), 12.5 (1H, b) | | |
| 1014 | 1.0~2.0 (14H, m), 2.2~2.6 (2H, m), 2.84 (3H, s), 3.00 (2H, q, J=7), 3.4~4.6 (3H, m), 6.9~7.4 (3H, m), 12.5 (1H, b) | | |
| 1015 | 1.0~2.0 (14H, m), 1.37 (3H, t, J=7), 2.3~2.7 (2H, m), 2.97 (2H, q, J=7), 3.4~4.6 (7H, m), 6.9~7.4 (3H, m), 13.0 (1H, b) | | |
| 1029 | 1.0~2.0 (m, 10H), 1.37 (t, 3H, J=7), 2.0~2.7 (m, 6H), 2.62 (s, 3H), 3.2~4.5 (m, 3H), 7.0~7.3 (m, 3H), 12.0 (b, 1H) | | |
| 1034 | 1.0~2.1 (14H, m), 2.3~2.6 (2H, m), 2.61 (3H, s), 3.4~4.6 (7H, m), 6.9~7.4 (3H, m), 12.0 (1H, b) | | |
| 1035 | 1.0~2.1 (14H, M), 1.37 (3H, t, J=7), 2.2~2.4 (2H, m), 2.84 (3H, s), 3.0 (2H, q, J=7), 3.4~4.6 (3H, m), 6.9~7.4 (3H, m) | | |
| 1036 | 1.27 (3H, t, J=7), 1.6~2.0 (4H, m), 2.36 (2H, t, J=7), 2.85 (3H, s), 3.9~4.3 (4H, m), 7.0~7.3 (3H, m), 12.0 (1H, b) | | |
| 1037 | 1.7~2.1 (4H, m), 2.40 (3H, s), 2.42 (2H, t, J=7), 4.02 ((2H, t, J=7), 7.0~7.4 (3H, m), 11.0 (1H, 6). | | |

TABLE 13

| Comp. No. | N.M.R. $\delta_{CDCL_3}^{TMS}$P.P.M. | Mass (CI) | TLC |
|---|---|---|---|
| 914 | 1.18 (t, 3H, CH₃), 1.98 (q, 2H, CH₂), 2.4~2.6 (t, 2H, CH₂), 4.07 (q, 2H, CH₂), 7.2~7.3 (m, 3H, phenyl proton), 8.15 (s, 1H, CH) 12.2 (b.s, 1H, NH) | 277 | Rfb = 0.52 |
| 938 | 1.96 (q, 2H, CH₂), 2.39 (t, 2H, CH₂), 4.05 (t, 2H, CH₂), 7.2~7.3 (m, 3H, phenyl proton), 8.16 (s, 1H, CH) | | |
| 955 | 1.99 (2H, q, J = 7), 2.39 (3H, s), 2.40 (2H, t, J = 7), 4.03 (2H, t, J = 7), 7.0~7.4 (3H, m), 11.5~12.5 (1H, b) | 263 176 | |
| 956 | 1.22 (3H, t, J = 7), 2.00 (2H, q, J = 7), 2.41 (2H, t, J = 7), 2.80 (2H, q, J = 7), 4.05 (2H, t, J = 7), 7.0~7.4 (3H, m), 12.5 (1H, s) | 277 | |
| 957 | 0.97 (3H, t, J = 7), 1.72 (2H, q, J = 7), 1.99 (2H, q, J = 7), 2.76 (2H, t, J = 7), 4.06 (2H, t, J = 7), 7.0~7.4 (3H, m), 12.62 (1H, b.s) | 291 176 | |
| 958 | 0.92 (3H, t, J = 7), 1.2~2.2 (6H, m), 2.40 (2H, t, J = 7), 2.78 (2H, t, J = 7), 4.04 (2H, t, J = 7), 7.0~7.4 (3H, m), 12.8 (1H, s) | 176 | |
| 959 | 0.87 (3H, t, J = 7), 1.2~2.2 (10H, m), 2.40 (2H, t, J = 7), 2.77 (2H, t, J = 7), 4.04 (2H, t, J = 7), 7.0~7.4 (3H, m), 12.5 (1H, b.s) | 336 176 | |
| 960 | 0.85 (3H, t, J = 7), 1.0~2.2 (16H, m), 2.40 (2H, t, J = 7), 2.77 (2H, t, J = 7), 4.04 (2H, t, J = 7), 7.0~7.4 (3H, m), 12.5 (1H, b.s) | 375 267 176 | |
| 961 | 0.85 (3H, t, J = 7), 1.0~2.2 (22H, m), 2.40 (2H, t, J = 7), 2.77 (2H, t, J = 7), 4.04 (2H, t, J = 7), 7.0~7.4 (3H, m), 12.6 (1H, b.s) | 445 359 262 176 | |
| 962 | 0.85 (3H, t, J = 7), 1.0~2.2 (26H, m), 2.40 (2H, t, J = 7), 2.77 (2H, t, J = 7), 4.04 (2H, t, J = 7), 7.0~7.4 (3H, m), 12.5 (1H, b.s) | 445 259 262 176 | |
| 963 | 0.85 (3H, t, J = 7), 1.0~2.2 (30H, m), 2.40 (2H, t, J = 7), 2.77 (2H, t, J = 7), 4.04 (2H, t, J = 7), 7.0~7.4 (3H, m), 12.5 (1H, b.s) | 473 445 262 176 | |
| 964 | 2.02 (2H, q, J = 7), 2.42 (2H, t, J = 7), 4.08 (2H, t, J = 7), 7.1~7.6 (5H, m), 8.2~8.5 (2H, m), 12.8 (1H, b.s) | 325 | |

What is claimed is:
1. A compound of the formula

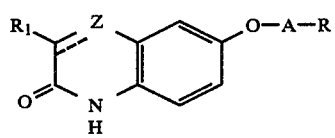

wherein Z is N or NH, --- is a single or double bond, $R_1$ is hydrogen, $C_{1-20}$ alkyl or optionally substituted phenyl, A is lower alkylene, R is carboxyl, lower alkoxycarbonyl,

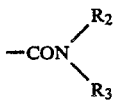

or 1-cycloalkyl-tetrazole-5-yl, $R_2$ is lower alkyl, hydroxy-lower alkyl or optionally substituted phenyl-lower alkyl, $R_3$ is lower alkyl or cycloalkyl, or $R_2$ and $R_3$ together constitute

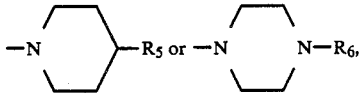

and $R_5$ and $R_6$ are hydrogen or optionally substituted phenyl, or a pharmacologically acceptable salt thereof.

UNITED STATES PATENT AND TRADEMARK OFFICE
CERTIFICATE OF CORRECTION

PATENT NO. : 4,870,175
DATED : September 26, 1989
INVENTOR(S) : Yukio SUZUKI et al.

It is certified that error appears in the above—identified patent and that said Letters Patent is hereby corrected as shown below:

In column 9, Table 1, change Compound No. "974" to --947--.

In columns 33-34, Table 12, Compound 920, change "Rfb = 0.52" to --Rfb = 0.50--;

In columns 33-34, Table 12, Compound 921, change "7CH3)," to --7CH2),--; change Mass "734" to --372--; change "Rfb = 0.56" to --Rfb = 0.54--.

In columns 35-36, Table 12, Compound 967, change "1.17" to --1.12--.

In columns 37-38, Table 12, Compound 991, change Mass "463" to --468--.

In columns 37-38, Table 13, Compound 958, before Mass "176" insert Mass --305--.

Signed and Sealed this

Eighth Day of January, 1991

Attest:

HARRY F. MANBECK, JR.

*Attesting Officer*  *Commissioner of Patents and Trademarks*